US011241244B2

United States Patent
Jaffe et al.

(10) Patent No.: US 11,241,244 B2
(45) Date of Patent: Feb. 8, 2022

(54) CATHETER AND A RETRIEVAL SYSTEM USING THE CATHETER

(71) Applicant: MOR RESEARCH APPLICATIONS LTD., Tel Aviv (IL)

(72) Inventors: Ronen Jaffe, Moshav Yaad (IL); Eytan Jaffe, Alon Hagalil (IL)

(73) Assignee: MOR RESEARCH APPLICATIONS LTD., Tel Aviv (IL)

( * ) Notice: Subject to any disclaimer, the term of this patent is extended or adjusted under 35 U.S.C. 154(b) by 552 days.

(21) Appl. No.: 15/962,285

(22) Filed: Apr. 25, 2018

(65) Prior Publication Data
US 2018/0235644 A1 Aug. 23, 2018

Related U.S. Application Data

(63) Continuation of application No. PCT/IB2016/056420, filed on Oct. 25, 2016.

(60) Provisional application No. 62/246,138, filed on Oct. 26, 2015.

(51) Int. Cl.
*A61B 17/221* (2006.01)
*A61B 17/22* (2006.01)
*A61M 25/10* (2013.01)

(52) U.S. Cl.
CPC ...... *A61B 17/221* (2013.01); *A61B 17/22032* (2013.01); *A61B 2017/2215* (2013.01); *A61B 2017/22034* (2013.01); *A61B 2017/22054* (2013.01); *A61B 2017/22067* (2013.01); *A61B 2017/22079* (2013.01); *A61B 2217/005* (2013.01); *A61M 2025/1059* (2013.01)

(58) Field of Classification Search
CPC ............ A61B 17/221; A61B 17/22032; A61B 2017/22034; A61B 2017/22054; A61B 2017/22079; A61B 2017/2215; A61B 2217/005; A61M 2025/1059; A61M 2025/0018

See application file for complete search history.

(56) References Cited

U.S. PATENT DOCUMENTS

| | | | | |
|---|---|---|---|---|
| 5,275,605 A | * | 1/1994 | Winkler | A61B 17/22 604/908 |
| 5,389,080 A | * | 2/1995 | Yoon | A61B 17/3421 604/167.03 |
| 5,484,412 A | * | 1/1996 | Pierpont | A61M 25/104 604/101.03 |
| 5,634,937 A | * | 6/1997 | Mollenauer | A61B 17/00234 604/115 |

(Continued)

FOREIGN PATENT DOCUMENTS

WO 2016010995 A1 1/2016

OTHER PUBLICATIONS

International Search Report dated Jan. 17, 2017 for International Application No. PCT/IB2016/056420 filed Oct. 25, 2016.

*Primary Examiner* — Katherine M Rodjom
(74) *Attorney, Agent, or Firm* — Blue Filament Law PLLC

(57) ABSTRACT

A catheter for removable insertion into a body vasculature has at least one inflatable member. The catheter has at least in part an expandable body that forms an internal axially extending lumen in at least the expanded state of the body. The inflatable member is adjacent a distal axial end of the body and is configured to at least partially obstruct the lumen.

12 Claims, 22 Drawing Sheets

(56) References Cited

U.S. PATENT DOCUMENTS

| | | | | |
|---|---|---|---|---|
| 5,868,753 | A | * | 2/1999 | Schatz .................. A61F 2/95 606/108 |
| 8,795,305 | B2 | | 8/2014 | Martin et al. |
| 2001/0051810 | A1 | * | 12/2001 | Dubrul ................ A61B 17/221 606/159 |
| 2002/0072764 | A1 | | 6/2002 | Sepetka et al. |
| 2002/0099396 | A1 | * | 7/2002 | Slaker ............... A61M 25/1006 606/159 |
| 2005/0085826 | A1 | | 4/2005 | Nair et al. |
| 2006/0030865 | A1 | | 2/2006 | Balg |
| 2012/0041474 | A1 | | 2/2012 | Eckhouse et al. |
| 2013/0079796 | A1 | | 3/2013 | Slee et al. |
| 2013/0304082 | A1 | * | 11/2013 | Aklog ................ A61B 17/3207 606/127 |
| 2014/0171958 | A1 | * | 6/2014 | Baig ................ A61B 17/22032 606/108 |
| 2014/0309655 | A1 | | 10/2014 | Gal et al. |
| 2016/0015403 | A1 | * | 1/2016 | Nguyen ............... A61B 17/221 606/127 |

* cited by examiner

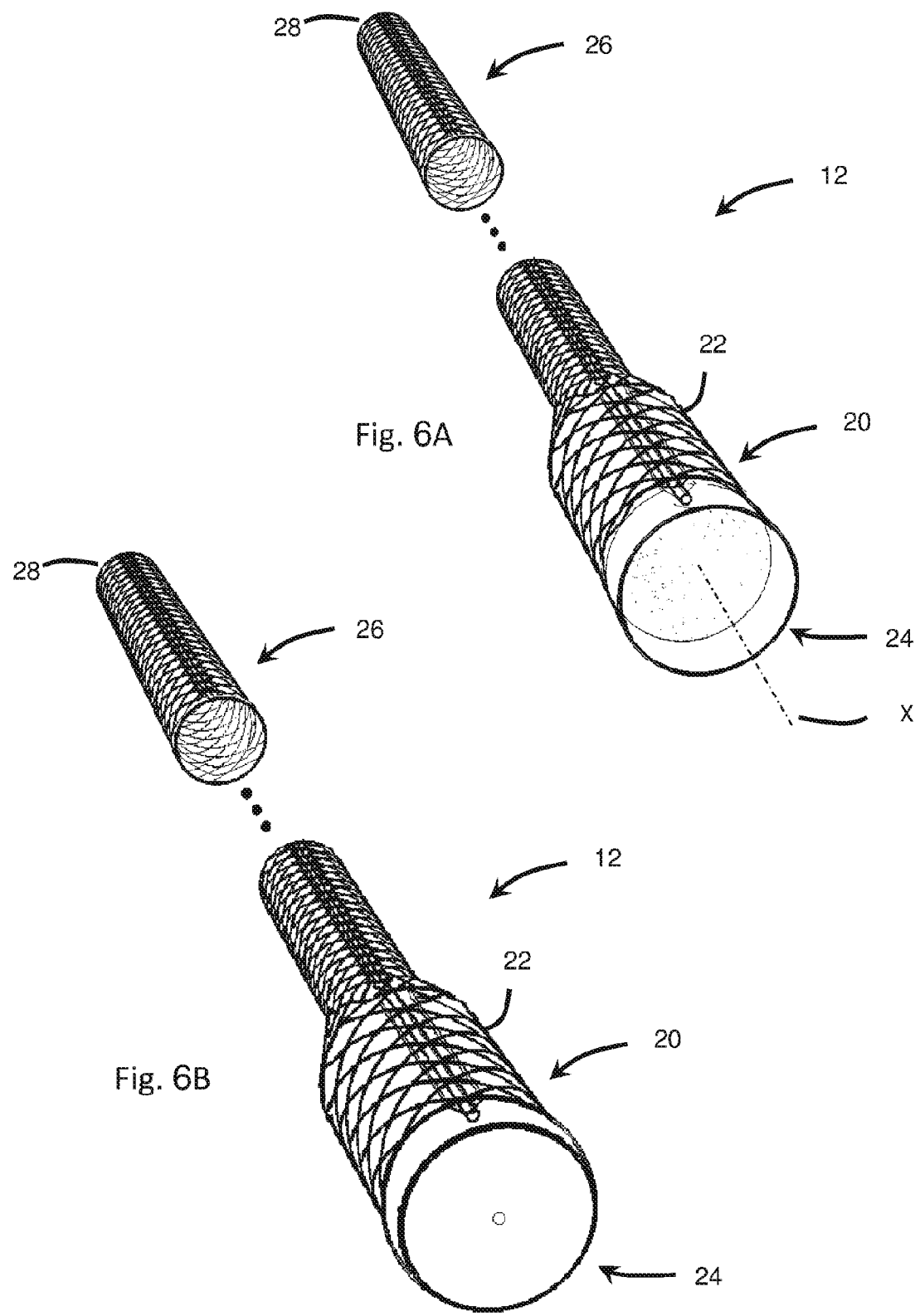

CATHETER AND A RETRIEVAL SYSTEM USING THE CATHETER

RELATED APPLICATIONS

This application is a continuation of PCT Application Serial Number PCT/IB/2016/056420 filed 25 Oct. 2016 that in turn claims priority benefit of U.S. Provisional Application Ser. No. 62/246,138 filed 26 Oct. 2015; the content of which are hereby incorporated by reference.

TECHNICAL FIELD

Embodiments of the invention relate to a catheter and a system and/or method for retrieval and/or assistance in retrieval of obstructions from a body vasculature using the catheter.

BACKGROUND

Such catheter, system and/or method may find usability in various therapeutic procedures within a body vasculature, such as in removing blockages in body lumens while providing safety means and/or measures for ensuring safe retrieval of such blockages.

In therapeutic procedures provided for example during an acute ischemic stroke it is an aim to preserve tissue in the ischemic penumbra, where perfusion is decreased. Tissue in this area can be preserved by restoring blood flow to the compromised area. Methods available for this purpose may include administration of thrombolytic agents such as recombinant tissue-type plasminogen activator and intra-arterial approaches, that attempt to establish revascularization so that cells in the penumbra can be rescued before irreversible injury occurs.

Restoring blood flow can mitigate the effects of ischemia only if performed quickly, and various pharmacological and endovascular techniques have been studied in the treatment of acute ischemic stroke.

US2013079796 describes a method for restoring blood flow in occluded blood vessels using an apparatus having a self-expandable distal segment that is pre-formed to assume a superimposed structure in an unconstrained condition but can be made to take on a volume-reduced form making it possible to introduce it with a micro-catheter and a push wire arranged at the proximal end.

US2012041474 describes a clot removal device including a tubular clot capture element having a first internal diameter and a clot engaging element having a second external diameter. The first diameter and the second diameter may be selected to permit the clot engaging element to be rotated within the tubular clot capture element. U.S. Pat. No. 8,795,305 describes a device for removing obstructions from body lumens. The device assists in clearing blockages within the vasculature, by using a cover configured to enclose an obstruction to assist in its safe removal from the body.

SUMMARY

The following embodiments and aspects thereof are described and illustrated in conjunction with systems, tools and methods which are meant to be exemplary and illustrative, not limiting in scope.

In an embodiment there is provided a catheter for removable insertion into a body vasculature, the catheter includes at least one inflatable member and at least part of the catheter includes an expandable body, wherein the expandable body forming an internal axially extending lumen at least in expanded states of the body and the at least one inflatable member being adjacent a distal axial end of the body and being configured to at least partially obstruct the lumen, for example by inflation into the lumen.

In certain cases, in addition or in alternative to obstructing the lumen by inflation into the lumen the inflatable member may be on an outer side of the body and when inflated, urge or bias the body to flex radially inwards to at least partially obstruct the lumen.

In an embodiment, the expandable body is self-expanding to assume the expanded state, for example by being elastically self-expandable. Other forms of expanding the body may be by internal means such as an internal balloon that is inflated to expand the catheter and then removed out of the catheter's lumen.

In an embodiment, the at least one inflatable member includes semi-compliant and/or compliant material, for example exhibiting at least in body temperature a diameter growth of about 10% and/or higher when inflated, and preferably about 20% and/or higher when inflated. Such semi-compliant and/or compliant material, may in addition or instead be defined for example by exhibiting at least in body temperature a Burst Strength Pressure of up to about 300 psi (20 atm), and preferably up to about 30 psi (2 atm).

In an aspect of the invention, at least certain catheter embodiments may be designed to be used within various sized bodily lumens, for example, ranging from about 2 to about 6 millimeters in diameter. Therefore, inflatable member(s) used for closing internal lumens of such catheter's should preferably be on the one hand flexible enough to assume various sizes when inflated, while on the other hand avoid exertion of outer directed radial forces that may harm or damage the bodily vessels within which they are inflated. It is therefore proposed that for such catheter embodiments, suitable inflatable members at least in certain cases may be of a relative 'compliant' nature that can assume relative large diameter growth ratio in response to low inflation pressure.

Inflatable member(s) includes semi-compliant and/or compliant material(s) may be characterized by having or requiring a low pressure for inflation, possibly of about 2 atmospheres or less, preferably 1 atmosphere or less. Such low pressure and high compliant inflatable member(s) may be advantageous in reducing risk of e.g. damage occurring to blood vessels in which such inflatable member(s) are inflated. In at least certain embodiments the inflatable member(s) may be defined as being semi-compliant (or preferably compliant) and elastomeric. In certain embodiments, low-pressure elastomeric balloons, which are inflated by volume, not pressure; can stretch 100-600%.

Semi-compliant or compliant materials for the inflatable member(s), in an aspect of the invention may permit on the one hand to obstruct or partially obstruct an inner lumen of the catheter, preferably of the catheter's casing, while limiting outer radial directed forces applied upon walls of a bodily lumen such as a blood vessel so as to limit damage to those walls. In addition or in alternative, inflatable member(s) including semi-compliant or compliant materials once inflated typically take a path of least resistance for example along an axis of the catheter once again limiting outer directed radial forces that may harm the blood vessel's wall.

In an embodiment, the at least one inflatable member includes an outer portion and an inner portion, wherein the inner portion being configured to inflate into the lumen during inflation of the inflatable member, wherein possibly the inner and/or outer portions are films/membranes, further possibly made from different materials.

In an embodiment, the inner portion is from more compliant material than the outer portion, for example the inner portion being from semi-compliant and/or compliant material and the outer portion from non-compliant material. Such embodiment may provide for an inflatable member having an outer stiffer and less expandable/inflatable portion while including an inner more compliant portion with an increased inflation ratio that has a higher inflation ratio than the outer portion for a generally similar inflation pressure.

In an embodiment, the at least one inflatable member comprises at least one seam portion dividing the inflatable member into segments. Such division into segments may increase the ability of the inflatable member to inflate radially inwardly; and for example in embodiments where the inflatable member is formed along substantially the entire periphery of the catheter to inflate inwardly to meet itself.

In an embodiment, in a contracted non-expanded state of the body, the inflatable member in a deflated state being formed with pleats, for example on an inner side of the inflatable member configured to face into the lumen. Such pleat type formations permit compact packing of the inflatable member that is configured on the one hand to be compact and go along with a low profile preferably required for delivery of the catheter, while on the other hand in an expanded state of the catheter's body provide sufficient material for permitting at least partial obstruction of the caterer's inner lumen.

In accordance with at least certain embodiments of the invention there is also provided a method for retrieving matter, possibly an obstruction causing an ischemic stroke in a body vasculature, from a body vasculature including the steps of: providing a catheter comprising at least one inflatable member and an internal lumen opening out via an opening of the catheter at a distal end of the catheter, placing the catheter in a deployed state within the body vasculature with its distal end upstream of the matter, urging the matter into the catheter's lumen via the opening, and inflating the at least one inflatable member to at least partially plug the opening and/or a portion of the lumen adjacent the opening.

In an embodiment, the method can include a step of activating suction in an upstream proximal direction through the internal lumen of the catheter at least after deployment of the catheter with its distal end upstream of the matter. Such suction may be permitted by provision of sealing membranes or films upon the catheter's body that funnel suction activated from upstream, typically from outside of the body by a physician, through the catheter's internal lumen.

In addition to the exemplary aspects and embodiments described above, further aspects and embodiments will become apparent by reference to the figures and by study of the following detailed descriptions.

BRIEF DESCRIPTION OF THE FIGURES

Exemplary embodiments are illustrated in referenced figures. It is intended that the embodiments and figures disclosed herein are to be considered illustrative, rather than restrictive. The invention, however, both as to organization and method of operation, together with objects, features, and advantages thereof, may best be understood by reference to the following detailed description when read with the accompanying figures, in which:

FIGS. 6A and 6B schematically show perspective front views of at least certain catheter embodiments in at least partially unplugged and plugged states, respectively;

Figure 1A:
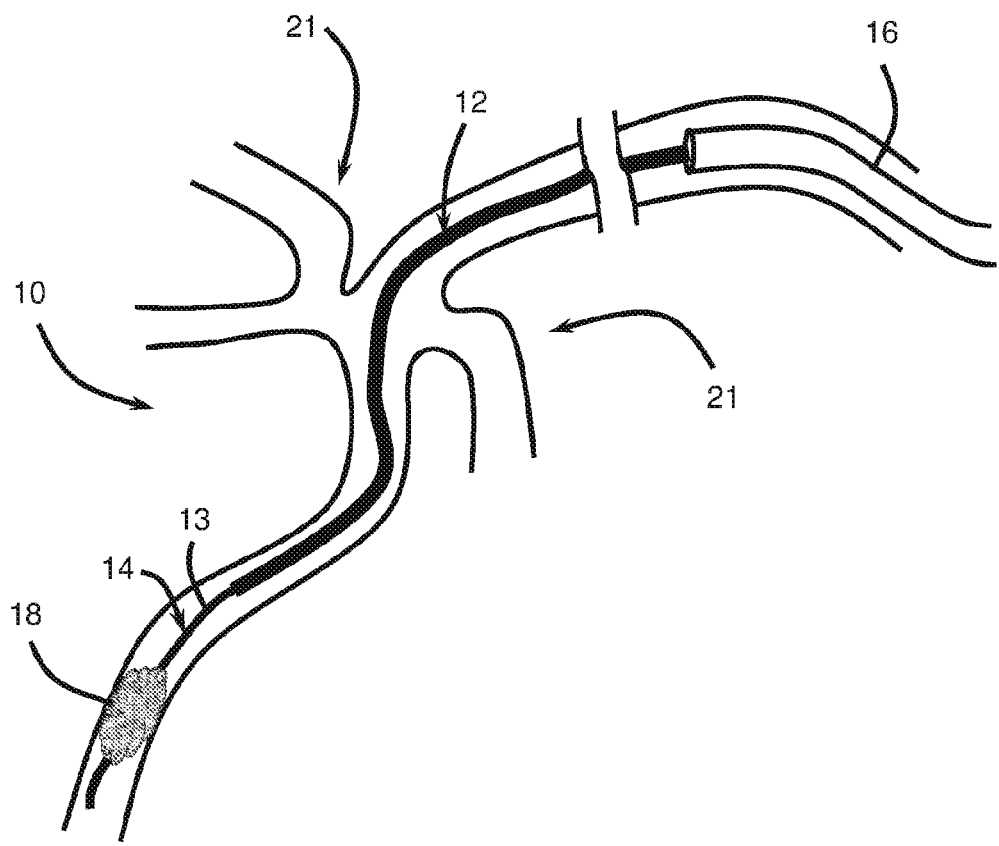
FIGS. 1A to 1I schematically show a system, method and/or catheter in accordance with at least certain embodiments of the present invention, during various steps of retrieval of blockage from a body lumen.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated within the figures to indicate like elements.

DETAILED DESCRIPTION

Attention is first drawn to FIGS. 1A to 1I showing a procedure and/or method performed by a physician in one possible form of the invention for accessing a cerebral vasculature of a human with a catheter 12 according to an embodiment of the invention, possibly enveloping or casing a device 14 for retrieval of an obstruction/clot 18 causing a blockage in a cerebral region 10 of the vasculature.

Catheter 12 in this exemplary configuration may be referred to as a so-called "intermediate catheter" since, as here shown, it can be located, at least in certain embodiments, in-between an inner device that may pass therethrough (such as a micro-catheter to which it can offer stability and/or support) and an outer device such as a guide catheter.

The procedure and/or method may first include advancing a guide catheter or long sheath 16 over a pre-deployed wire (not shown) from a distant part of the body (typically a limb) through the vasculature to a location possibly within vessels in the patients neck (typically the carotid artery). Through guide catheter 16, a catheter 12 according to various embodiments of the invention may be advanced preferably also over the pre-deployed wire into the cerebral region 10. A device 14 such as of a type including a stent retriever 15 for performing thrombectomy (i.e. clot removal) may then be advanced through catheter 12 in order to resolve an ischemic stroke and restore flow within the cerebral vasculature.

With regards to the aforementioned guide catheter (GC) and long sheath (LS)—it should be noted that typically such large-lumen tubes (as GC and LS) perform the same function. While a GC is inserted via a short sheath in a peripheral vessel, a LS functions like a GC but may be inserted into the vasculature without a different sheath—so that possibly there is a smaller hole in the peripheral vessel. Where reference herein may be made in this context to a GC it should be understood in at least most embodiments as being equally applicable to a LS.

Figure 1B:
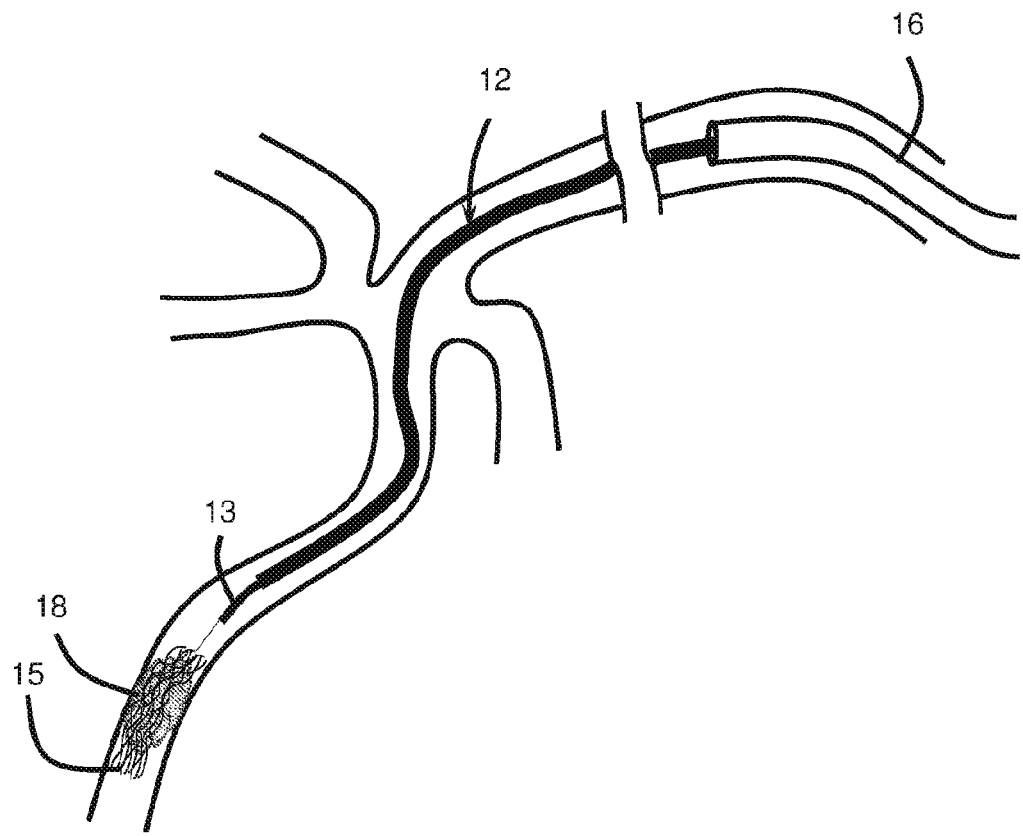
Figure 1C:
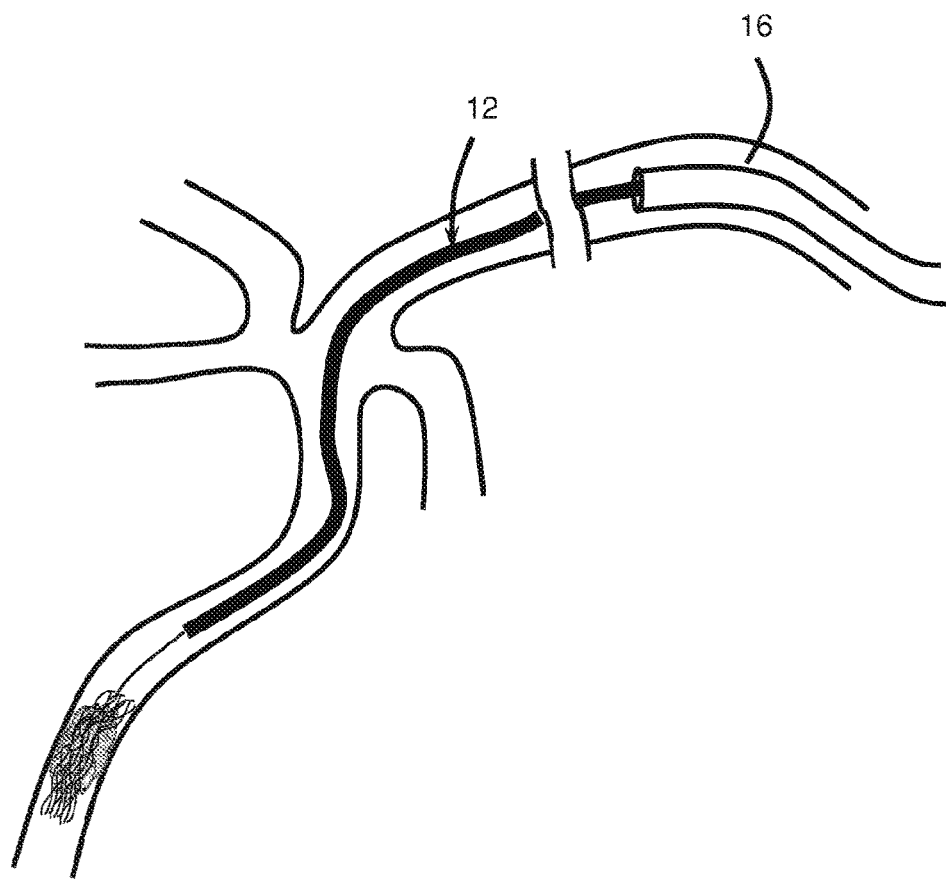
Figure 1D:
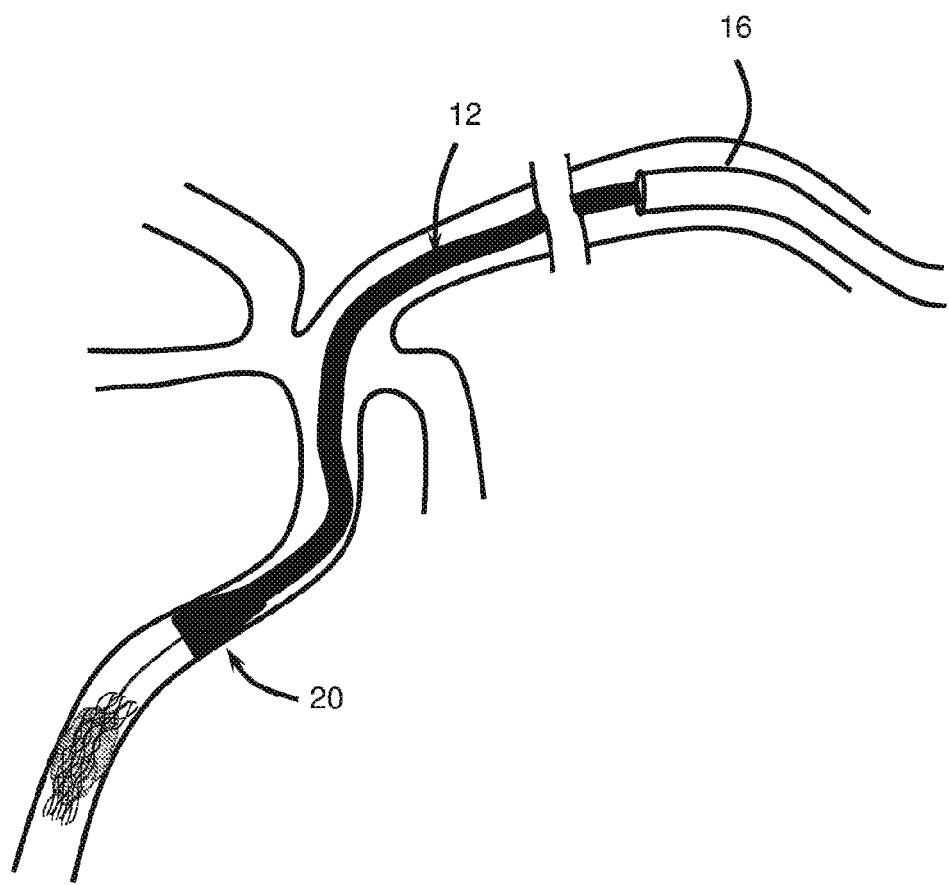
Figure 1E:
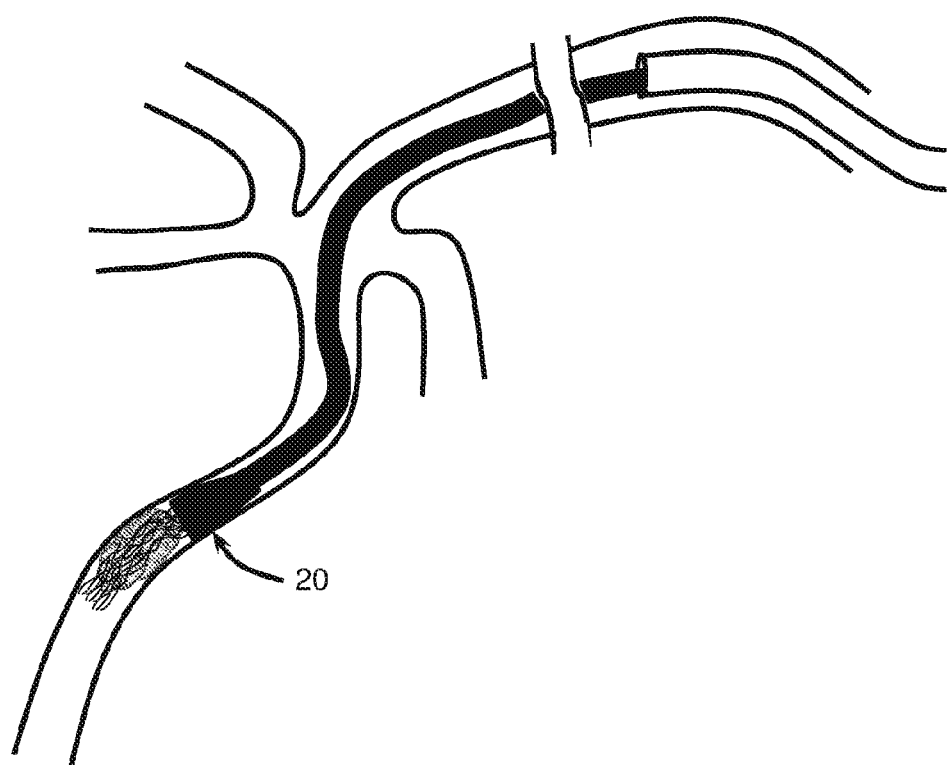
Figure 1F:
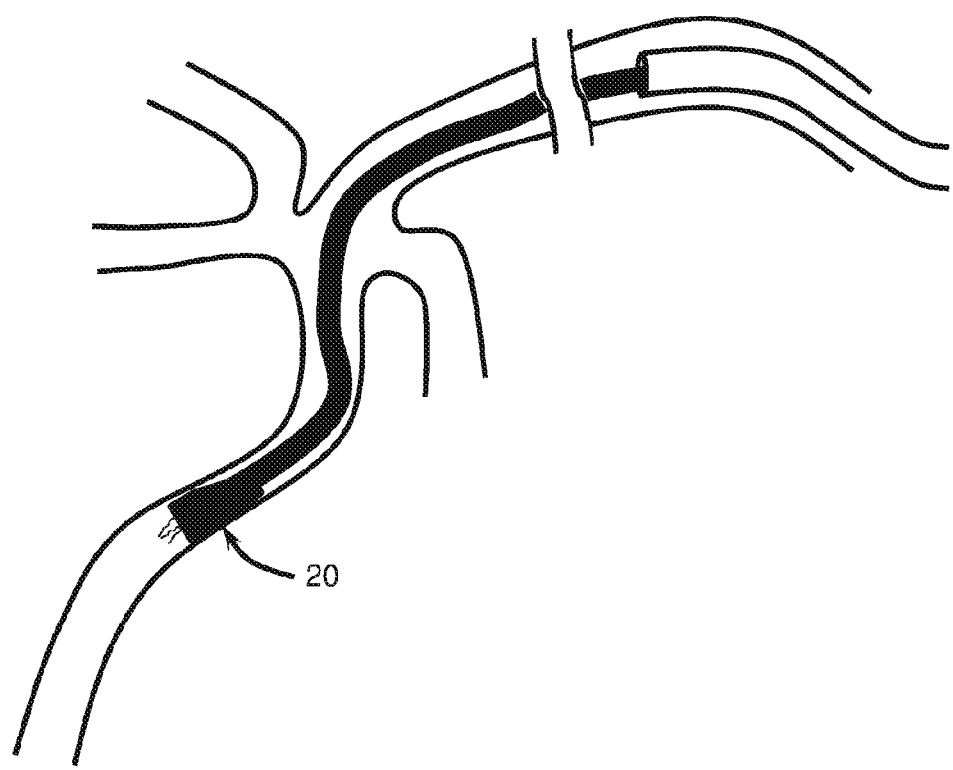

Device 14 may be advanced in a collapsed form to penetrate through obstruction 18 possibly protruding out of its distal side, and then a sheath or micro-catheter 13 constraining device 14 in the collapsed form may be pulled proximally by the physician to reveal stent 15 and allow it to expand and consequently be deployed in the obstruction (see FIG. 1B). Sheath 13 in some cases may be fully removed out of the body (see FIG. 1C). Herein the directional definition of "distal" refers to a "normal" flow direction of blood, and "proximal" to a direction that is opposite to the "normal" flow direction of blood.

In an aspect of the present invention, a casing 20 according to at least some embodiments of the invention may be included in a distal portion of catheter 12. Such casing 20 may be deployed to expand before, at, or after stent 15 has been deployed in obstruction 18. The physician in accordance with an embodiment of the invention may drag/pull obstruction 18 in a proximal direction towards and into casing 20 (see FIGS. 1E and 1F) and once within the casing (preferably fully within the casing—a step just after that seen in FIG. 1F), casing 20 may be distally activated to enclose on obstruction 18 and stent 15 and/or plug/seal at least parts of its distal open end to enclose e.g. obstruction 18 and stent 15 therein (see exemplary illustrating in FIG. 1G).

Figure 1G:
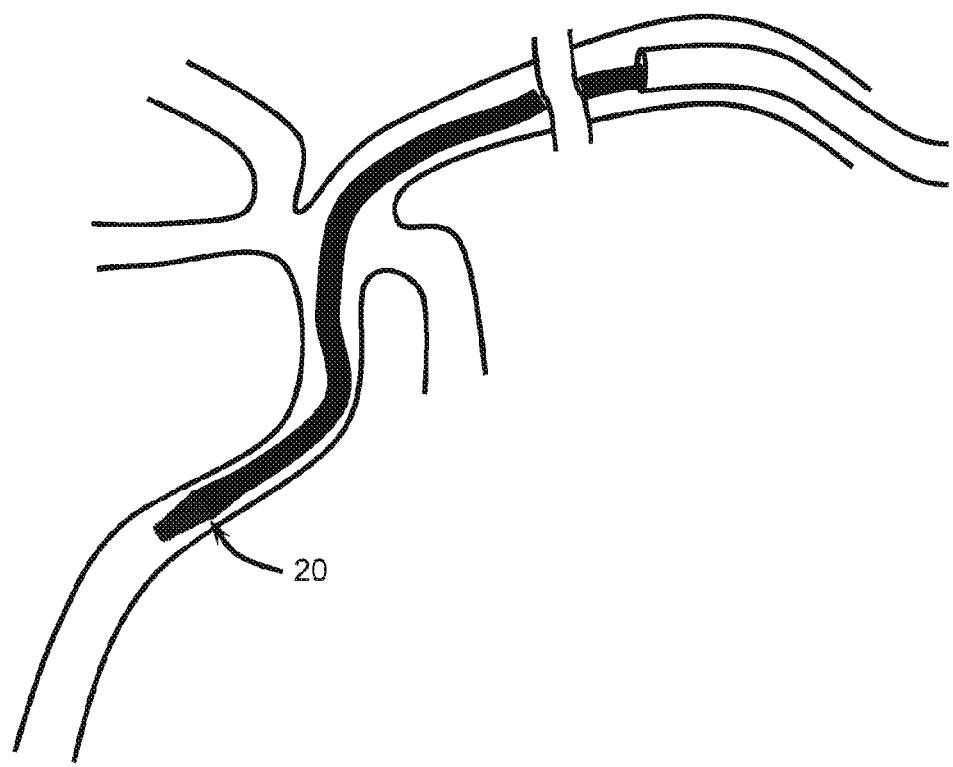
Figure 1H:
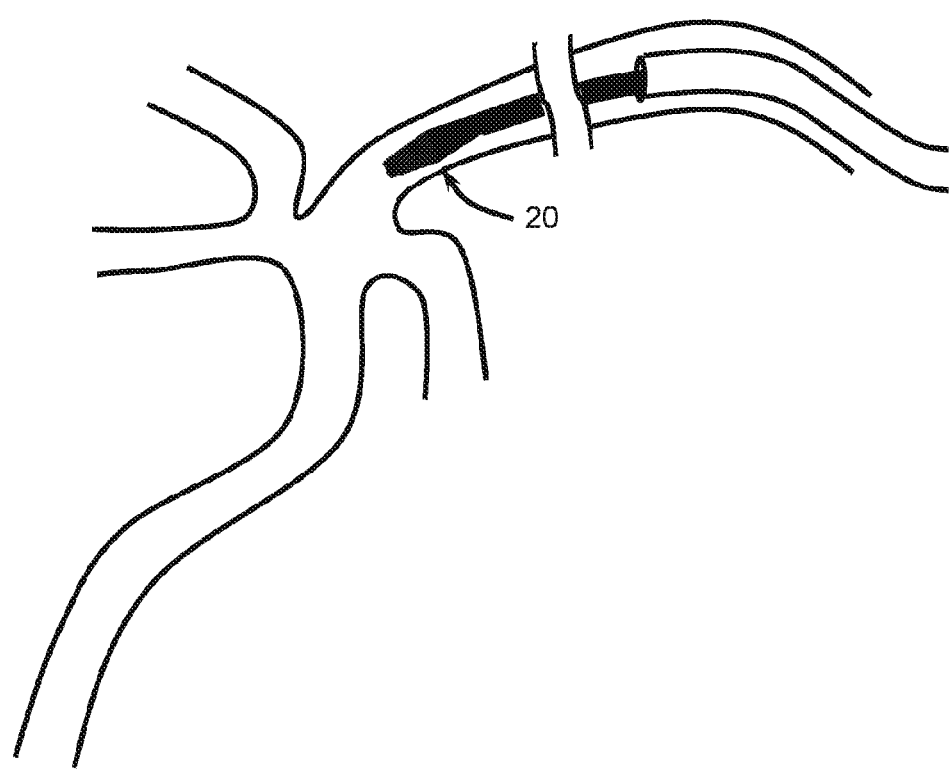
Figure 1I:
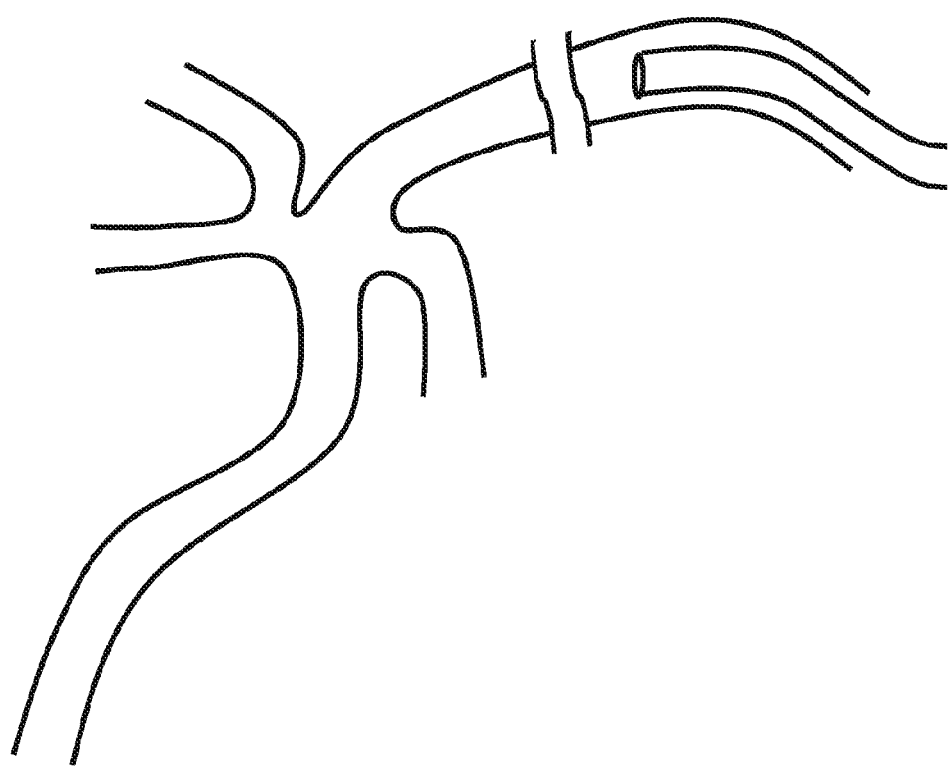

It is noted that while casing 20 e.g. in the illustration of FIG. 1G, during retrieval towards guide catheter (GC) or long sheath (LS) 16 is schematically shown as being slightly collapsed (e.g. radially inward and slightly distal from at least parts of the walls of the blood vessel)—in accordance with at least certain embodiments, the casing may not necessarily be collapsed along its full extension as here shown. In addition, the closing of casing 20 to enclose obstruction 18 and possibly stent 15 therein (as seen in FIGS. 1G and 1H) may not necessarily include formation of a tapering distal portion in the casing as here illustrated, but rather this distal portion may remain generally cylindrical while being closed by various measures as herein described.

Catheters 12 according to various embodiments of the invention may be deployed to remove and/or encase obstructions, such as obstruction 18, also without use of any additional retrieving devices such as stent retriever 15. Such removal may include locating an embodiment of the catheter with its casing 20 deployed proximal and upstream to the occlusion, and then activating suction urging fluid and obstructions (such as obstruction 18) in the blood vessel to be urged proximally upstream and into casing 20 for removal from the vasculature. Such suction may also be activated in conjunction with a retrieval device, such as device 15, to assist and/or ensure that all or most parts of the obstruction are sucked into the casing 20 for removal out of the patient's body.

For facilitating such suction, embodiments of the catheter 12 and casing 20 may be formed with means, e.g. membrane (s) or film(s), that substantially seal a periphery of the catheter and casing (e.g. seal between inner and outer sides of the catheter and casing). Such sealing permits the catheter 12 and its casing 20 when deployed within a blood vessel to act as a conduit for suction of a certain amount of blood (e.g. with obstructions present within the blood) in a proximal upstream direction via the distal open end of the catheter at the casing's distal end. Such sealing by e.g. membrane(s) of film(s) on at least a portion of the casing may be used also for blocking downstream flow through the blood vessel being treated when the sealed portion of the catheter (e.g. of the casing) is in contact with the blood vessel's wall. This may prevent distal embolization of particulate matter from occlusion 18.

In an aspect of the present technology, catheter 12 with its casing 20 effectively acts as a safety means (or safety mechanism), for cases e.g. where stent 15 may not sufficiently hold onto obstruction 18 as it drags the obstruction/ clot towards guide catheter/long sheath 16. In such a case, there is a risk that the clot or obstruction might be mobilized from its original blockage site, however while being translated through the bifurcations and tortuous anatomy might be migrated by e.g. blood flow into a branching vessel 21 at a bifurcation (see exemplary branching vessels 21 marked in FIG. 1A).

Figure 2A:
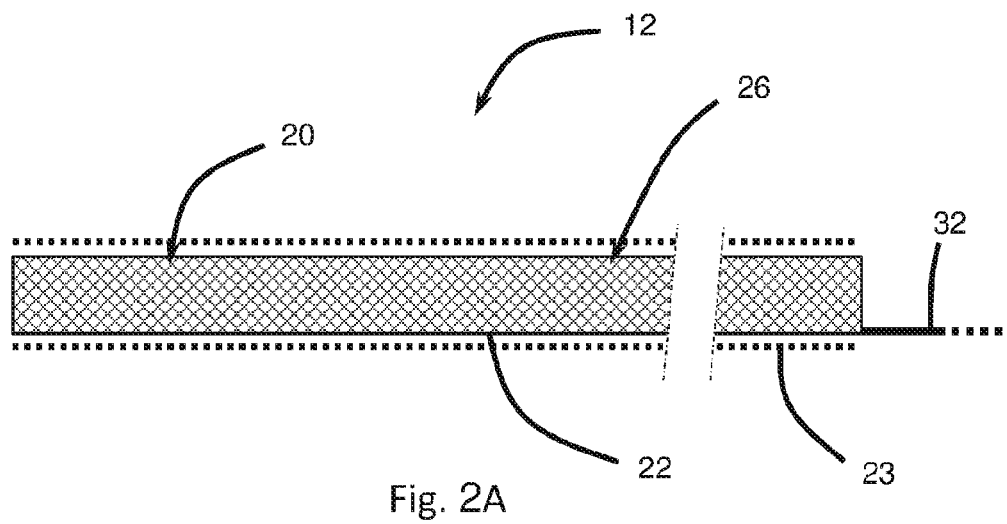
FIGS. 2A and 2B schematically show a side view of a catheter according to at least certain embodiments of the present invention, respectively, during delivery and when deployed in a bodily lumen.
Figure 2B:
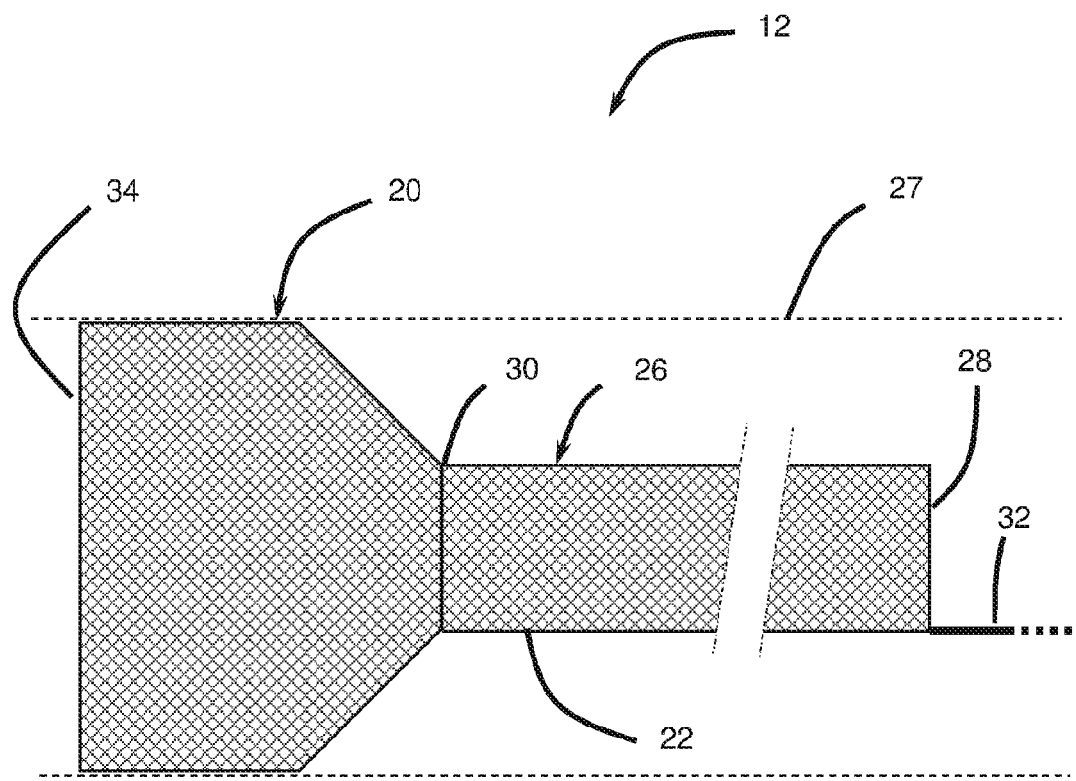

Attention is drawn to FIGS. 2A and 2B schematically showing a portion of an embodiment of catheter 12, here seen including an embodiment of a casing 20 located at a distal end/portion of a neck portion 26 of catheter 12. Catheter 12 includes a proximal end 28, at a proximal end of neck 26, and a merge 30 where neck 26 and casing 20 meet. In other words, catheter 12 here comprises a radially or latitudinally extendable casing (portion) and neck (portion). When extended, the casing and neck of the catheter form a funnel-like shape and the casing extends and narrows in a proximal direction to merge with a distal end of neck at a merge 30. FIGS. 2A and 2*b*, in particular with respect to casing and neck portion, are illustrative of both "rapid exchange" and non-"rapid exchange" (i.e. "over the wire") embodiments discussed herein.

A so-called "over the wire" catheter device is intended to travel the entire distance of a wire upon which it is delivered into the body, with the wire running through an inner lumen of the device from the distal tip to the proximal end. A so-called "rapid exchange" configuration is a design where a wire upon which the catheter delivered into the body, comes out of the catheter relatively close to the catheter's distal tip.

Neck portion 26 in some embodiments (not shown in FIGS. 2A and 2B) may be designed to optionally extend all the way along guide catheter 16 to outside of a patient being treated (e.g. outside of a limb or arm) when deployed with casing 20 adjacent an obstruction 18 to be removed. Thus in such embodiments, the catheter's proximal end 28 may be located outside of the patient and/or in communication with a hub (not shown) coupled to the catheter. Possibly, catheter 12 may be designed to have a "rapid exchange" configuration in which neck portion 26 may be designed to extend a shorter extent so that proximal end 28 may be located within guide catheter 16, possibly within a distal portion of guide catheter 16, when catheter 12 is deployed with casing 20 adjacent an obstruction 18 to be removed.

To permit suction of blood and/or obstructions upstream, embodiments of catheter 12 and casing 20, which are sealed at their periphery (by e.g. membrane(s) or film(s))—may include such sealing at least up to a position where catheter 12 enters guide catheter 16 (i.e. not necessarily up to proximal end 28 in "over the wire" catheter embodiments that extend all along the guide catheter). That is to say that embodiments where suction is performed at the catheter's distal end (at a distal end of casing 20), funneling of the suction towards upstream may be performed via catheter 12 until entering guide catheter 16 and from there upstream via guide catheter 16 itself, in particular in cases where catheter 16 is also sealed at its periphery. Alternatively, embodiments of the catheter may include such sealing along their entire axial extension up to proximal end 28 also in non-"rapid exchange" catheter embodiments (i.e. an "over the wire" design).

Catheter 12, in a "rapid exchange" configuration, may be designed to include a handle 32 extending in a proximal direction to outside of the patient from proximal end 28, to enable maneuvering of the neck 26 and casing 20 possibly in a proximal or distal direction by pulling or pushing by a physician. Casing 20 (in forms applicable to both "rapid exchange" and non-"rapid exchange" embodiments) as seen in this example may widen from merge 30 in a distal direction, possibly in a funnel shape having an open distal end 34 for receiving therein objects such as stent 15 and/or obstruction 18.

Catheter 12 may for example include a self-expanding body/mesh 22, possibly in a region of or including casing 20; and in some embodiments in regions of or including both casing 20 and neck 26. Said self-expanding body 22 may be formed of braided stainless steel wire or shape-memory alloy such as nitinol comprising e.g. approximately 50% nickel and 50% titanium and may have properties of shape memory and/or super-elasticity to elastically assume an expanded state at least when exposed to body temperature. The catheter's body or portions of the body in some embodiments (not shown) may also be urged to expand by other means such as an inflated balloon in its interior.

In FIG. 2A an outer sheath 23 is shown holding both casing 20 and neck 26 of catheter 12 in a contracted state with FIG. 2B showing catheter 12 in an expanded state of both casing 20 and neck 26 after removal of sheath 23. In some embodiments (not shown) only casing 20 may be held in a contracted state by constraining means or measures such as sheath 23, while neck 26 may be in an expanded/deployed state (if made from self-expanding material) during delivery of catheter 12 into the vasculature (e.g. here sheath 23 may be located possibly only on casing 20 while neck may remain during delivery in an expanded state). As seen in this example, at least casing 20 is configured to expand to place its outer periphery adjacent a lumen wall 27 of a body vasculature proximal to where e.g. an obstruction of said lumen to be removed is located. In an embodiment, casing 20 and possibly casing 20 together with neck 26 may be formed and/or coated with a sealed member such as a membrane of film so that when positioned in an expanded deployed state may block or stop downstream blood flow within lumen 27. Such membrane or film may be fluid impermeable and/or include materials, possibly polymeric material, such as silicone, urethane, polyethylene, polytetrafluoroethylene (PTFE), and the like.

In certain embodiments casing 20 and neck 26 may essentially form a unitary one piece construction. In an embodiment (not shown), said unitary one piece may be configured to expand, or be urged to assume, a substantially similar expanded outer diameter along its entire length (e.g. this length being or including of both casing 20 and neck 26). Since catheter 12 in certain embodiments may be formed from a body 22 of expandable elastic material; such expansion of catheter 12 in an outer radial direction, in portions located within guide catheter 16 may urge catheter 12 in such portions to bear (possibly in a sealing engagement) against the inner face of guide catheter 16 surrounding its lumen. As catheter 12 distally projects out of guide catheter 16 said catheter 12 by nature of its elasticity may gradually expand to assume a substantially similar outer expanded diameter, possibly as the inner surface of the vessel wall, along its remaining length up to distal end 34.

Catheter 12 may be delivered to a desired location e.g. in the cerebral vasculature—in a reduced diameter state covered by outer sheath 23 and proximal removal of sheath 23, possibly by pulling sheath 23 in a proximal direction by a physician, may enable body 22 to expand to its deployed expanded state in embodiments where body 22 or portions thereof are of a self-expanding nature. With attention drawn to FIGS. 1C and 1D, an example of expansion of catheter 12 due to removal of sheath 23 is seen, with catheter 12 being illustrated in a contracted state of both casing 20 and neck 26 in FIG. 1C while being illustrated in an expanded state in FIG. 1D after removal of sheath 23 that was present in FIG. 1C (although not marked).

In the expanded state, a portion of neck 26 (possibly adjacent proximal end 28 in the "rapid exchange" configuration of catheter 12); may be designed to bear against an inner wall of guide catheter 16 enclosing its internal lumen, in order to possibly at least partially seal against guide catheter 16 and/or anchor at least partially catheter 12 to guide catheter 16. In some embodiments, the expansion of neck 26 may be slightly smaller than the inner diameter of guide catheter 16 to enable sliding engagement of catheter 12 within guide catheter 16 during removal of catheter 12 from the body. Such sliding engagement may also be facilitated by coating(s), possibly lubricious coatings, provided on an outer periphery of catheter 12 reducing friction between catheter 12 and guide catheter 16.

Figure 3A:
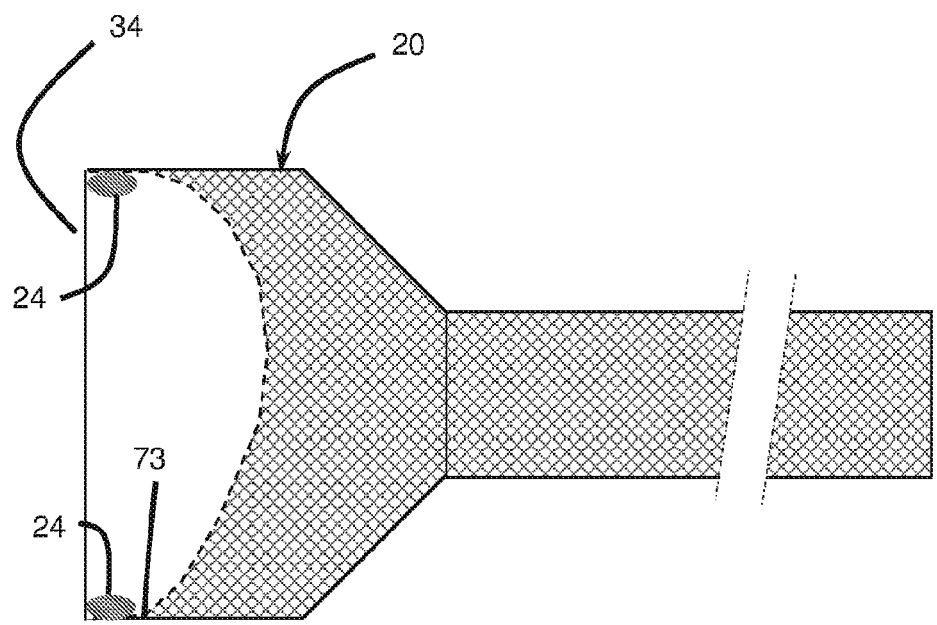
FIGS. 3A and 3B schematically show partial cross sectional side views of a catheter according to at least certain embodiments of the present invention, respectively, in unplugged/open and plugged/closed states.
Figure 3B:
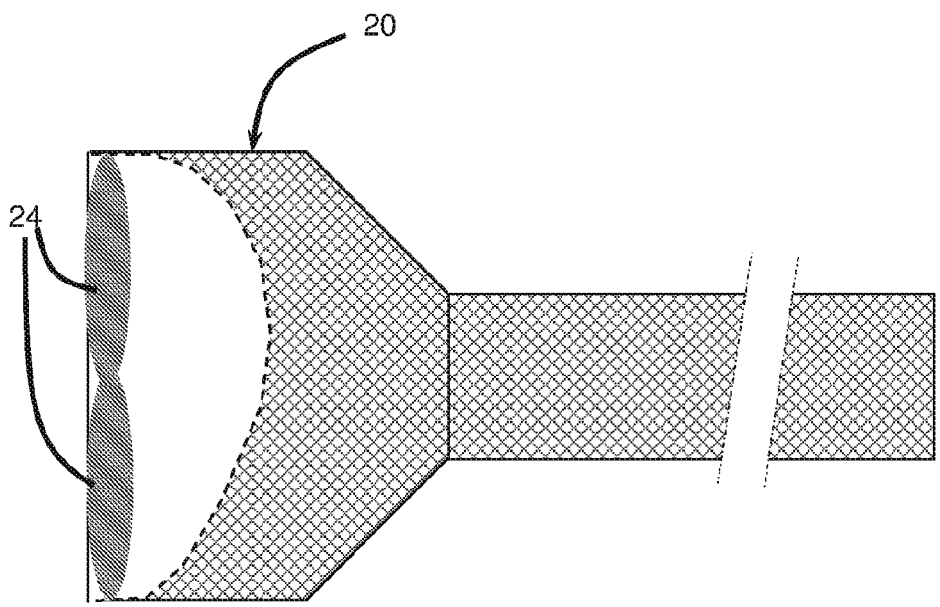

With attention drawn to FIGS. 3A and 3B an embodiment of casing 20 is schematically shown possibly including one or more inflatable member(s) 24; in this embodiment implemented by one or more inflatable balloon(s), taking any balloon form known for use in catheterization procedures, such as an angioplasty balloon, a ureteric balloon, or the like. Member(s) 24 may take any other form such as an inflatable membrane/film. The member(s) 24 are connected affixed, bonded and otherwise adhered to a wall of catheter 12, preferably of casing 20. Such connection may be to an inner and/or outer side or face of the wall. Inflation media or medium suitable for inflating various inflatable member embodiments of the invention may include at least one of: water, gaseous (possibly $CO_2$), saline (possibly sterile), contrast media and the like.

The one or more inflatable members 24 may be located at or adjacent a distal end 34 of catheter for plugging the catheter's open end, possibly after entry of an object such as obstruction 18 and/or stent 15 therein. In FIG. 3B, inflatable members(s) 24 are shown in inflated states plugging distal end 34. One or more radiopaque markers (not shown) may be positioned at various locations on catheter 12, preferably adjacent the member(s) 24 to assist in identifying that material such as obstruction 18 and/or stent 15 have entered into catheter 12 and passed the member(s) 24 and that such plugging may be activated. Such radiopaque markers comprise material that strongly absorbs X-rays and thus assists in proper placement e.g. of the catheter relative to the obstruction. Suitable radiopaque materials may include platinum, gold, iridium, tungsten, bismuth subcarbonate, barium sulfate, and others known to one of skill in the art.

An inner face 73 of catheter 12 defining its internal through-going lumen, preferably an inner face of at least a portion of catheter 12 including casing 20, may be coated with a slippery coating to facilitate passage of devices such as obstruction 18 and/or stent 15 through and/or into catheter 12 via distal end 34.

Possibly, channeling of medium for inflating members 34 may be via a tube (not shown) extending along catheter 12 from the inflatable members(s) 24 towards a location outside of the patient to be manipulated and/or activate for inflation/deflation by a physician. In a "rapid exchange" configuration of catheter 12, said tube may extend along casing 20 and neck 26 to proximal end 28 and from there via handle 32 possibly in this embodiment via a tube like handle to outside of the patient.

Figure 4A:
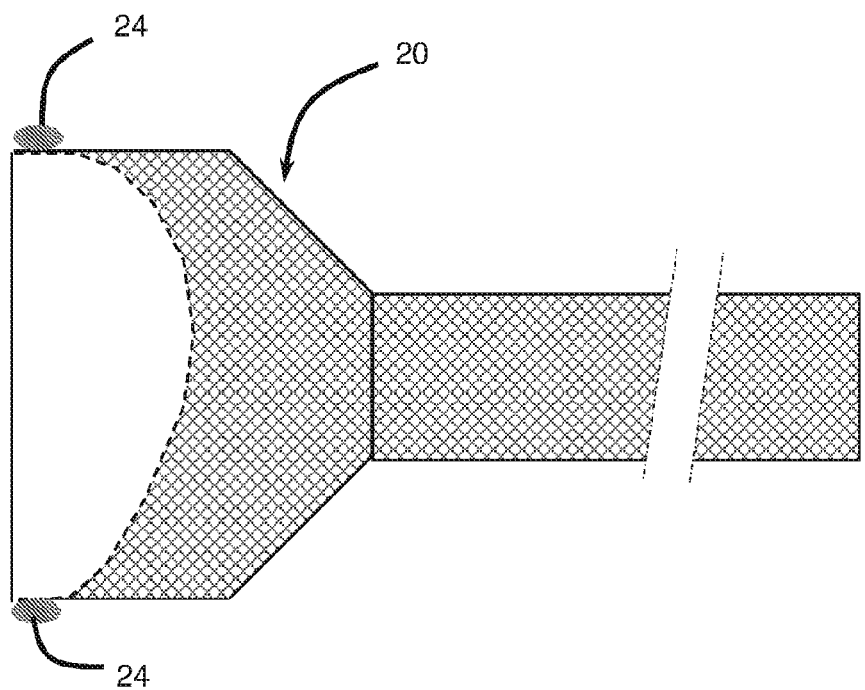
FIGS. 4A and 4B schematically show partial cross sectional side views of a catheter according to a further embodiment of the present invention, respectively, in unplugged and plugged states.
Figure 4B:
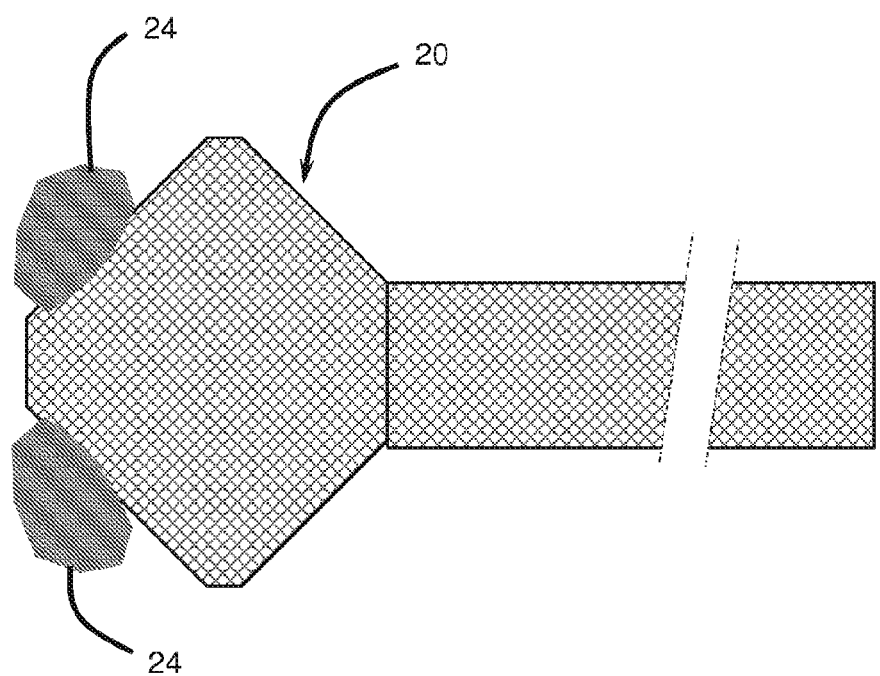

With attention drawn to FIGS. 4A and 4B a further embodiment of catheter 12 is schematically illustrated, here including inflatable member 24 on an outer side of a distal end of casing 20. Here inflation of member(s) 24 may urge a distal end of casing to contract against the elasticity of casing's body 22. In other words, the members 24 being confined by the dimensions of the vasculature are urged to expand inwardly against the outer surface of casing, which in turn causes the narrowing of the casing's distal portion and, hence, enclosing of the clot within the casing.

Figure 5A:
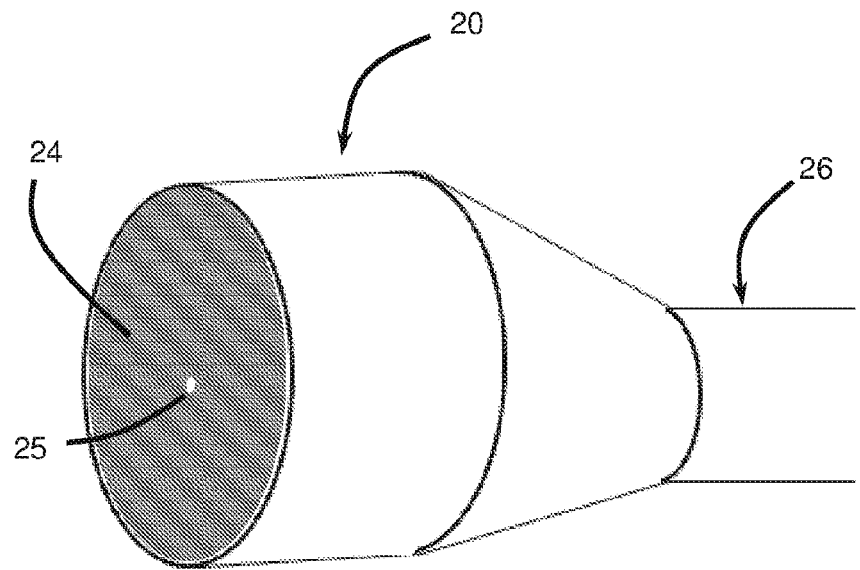
FIGS. 5A and 5B schematically show perspective front views of at least certain embodiments of a catheter of the present invention in a plugged state.
Figure 5B:
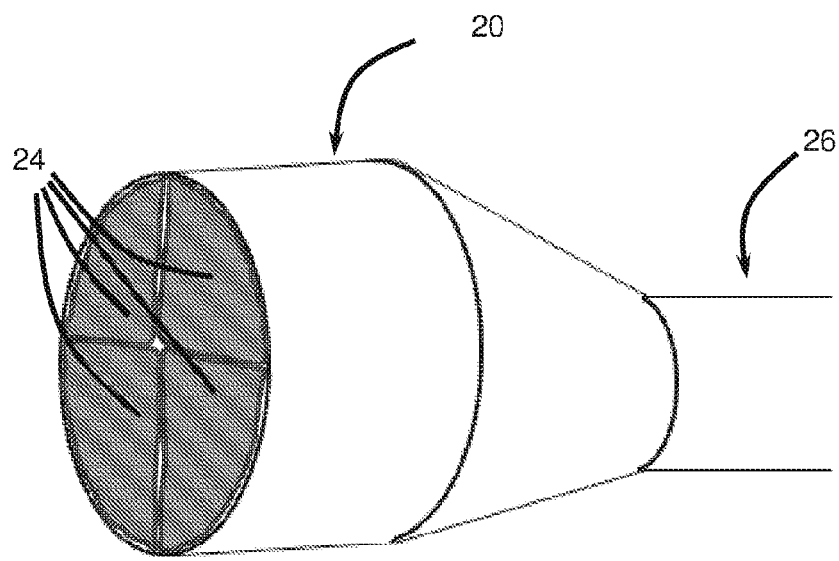

With attention drawn to FIGS. 5A and 5B, possible embodiments of catheter 12 from a direction aimed at open end 34 are schematically shown. In FIG. 5A, an embodiment including a single integral inflatable member 24 having in its inflated state a "holeless donut" configuration where portions of the member meets itself and seal at a center 25 of the "holeless donut". In FIG. 5A, several members 24, here optionally four, are shown plugging the catheter's distal end 34. The inflatable member(s) 24 may be kept in an inflated closed state during removal of an obstruction such as obstruction 18 from a bodily vessel (as discussed with respect to FIG. 1A to 1I).

Catheters according to at least some embodiments of the invention may be formed with inner and/or outer membranes or films formed on inner and/or outer sides of the catheter's body 22 (e.g. mesh). In a catheter embodiment having both inner and outer films, formation of such films may be performed by placing and/or forming the catheter's body 22 on a solid shaft that has been previously lined with a polymer inner liner (which constitutes an inner film of the catheter in the final catheter); and then sliding a polymer 'jacket' over the body and inner liner and melting the 'jacket' to collapse over the body and inner liner to form an outer film of the catheter, that is for example attached to the inner film. In at least some embodiments of the invention, the outer membrane attachment could be a thermal bond (lamination) if using a thermoplastic or may be bonded or mechanically attached if using thermoset. In a non-binding example, the inner and/or outer films formed on the catheter's body may range from about 0.012 to 0.05 millimeters in thickness.

Attention is drawn to FIGS. 6A and 6B illustrating a catheter 12 according to an embodiment of the invention extending and being formed about a longitudinal axis X. Catheter 12 here includes a neck portion 26 extending from a proximal end 28 of the catheter that is possibly outside of the patient or within a guide catheter in a "rapid exchange" configuration. From proximal end 28 the catheter extends up to a casing 20 at the catheter's distal end (the 'three dots' between supposedly "cut" portions of the catheter illustrating the catheter's long and continuous extension). Catheter 12 is here illustrated in an expanded deployed state, for example after removal of an external constraining sheath (or micro-catheter) in an embodiment including a self-expanding body (see, e.g., sheath 23 illustrated in FIG. 2) that kept the catheter in a contracted compact state during delivery to its place of deployment (e.g. proximal to an obstruction to be removed such as obstruction 18 in FIG. 1). In this example, casing 20 expanded to a larger radial size than neck portion 26 to form a funnel shape.

Catheter 12 accordingly for example has a self-expanding body/mesh 22, possibly in a region of, or including casing 20; and in some embodiments in regions of, or including both casing 20 and neck 26. The self-expanding body 22 may be formed of braided stainless steel wire or shape-memory alloy such as nitinol comprising e.g. approximately 50% nickel and 50% titanium and may have properties of shape memory and/or super-elasticity to elastically assume an expanded state at least when exposed to body temperature. Catheter 12 includes in addition an inflatable member 24 here at the casing's distal side that is configured for activation from an uninflated state seen in FIG. 6A to an inflated state seen in FIG. 6B.

Figure 7A:
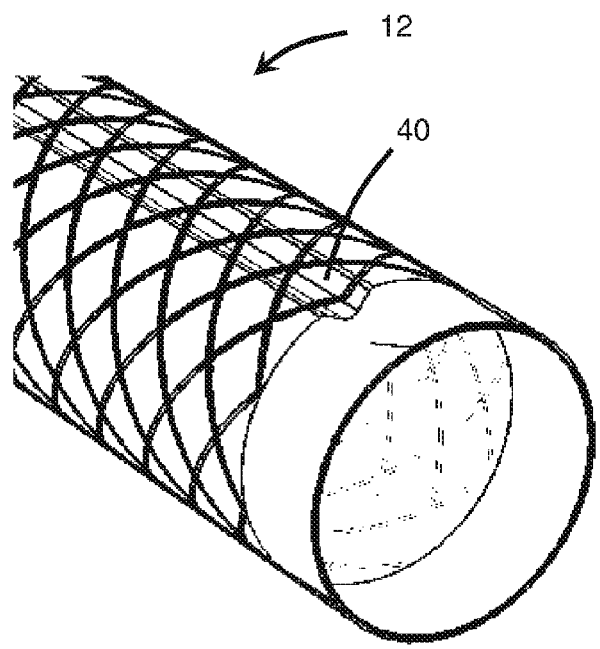
FIGS. 7A, 7B, 8A, 8B, 9, to 10 and 13, 14, 15A, 15B, 16, 17, 18, to 19 schematically show views of various catheter embodiments.
Figure 7B:
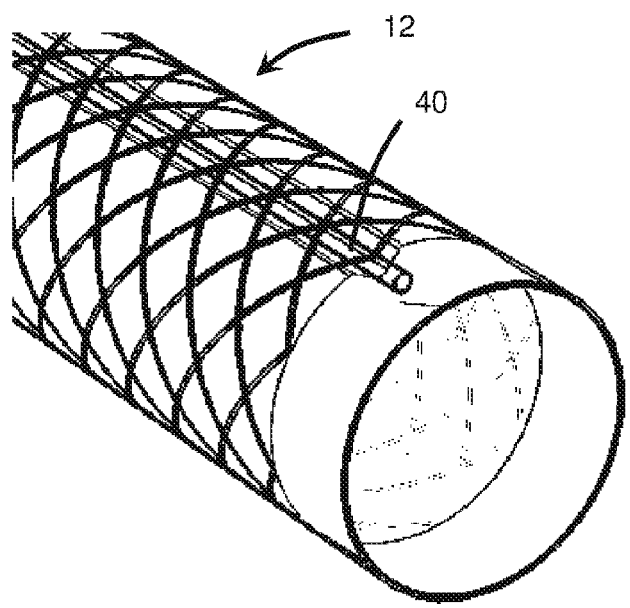

With attention drawn to FIGS. 7A and 7B several options of forming inflating lumens 40 (i.e. fluid feed lines) for inflating inflatable member(s) 24 are exemplified. In a first example (FIG. 7A), an inflating lumen 40 according to an embodiment of the invention may be formed along the catheter 12 between inner and outer films, which possibly encapsulate the catheter's mesh therebetween. Such inflation lumen 40 e.g. may be formed during the process of placing the aforementioned 'jacket' over the body and inner film; by locating a rod (possibly coated by PTFE/Teflon) in a space between the to be formed inner and outer films, and after melting the 'jacket' over the body and inner film (and rod), removing the rod to reveal the created inflation lumen 40. In a second example (FIG. 7B), an inflating lumen 40 according to an embodiment of the invention may be formed along the catheter 12 as an inflation tube formation, for example, that is separate from any film(s) formed on the catheter's body. Such inflation lumen in a tube-like formation may be formed on an inner or outer diameter of the catheter, and in a non-binding example may have a diameter of about 0.07 to 0.12 millimeters (if made e.g. from PET or polyamide) and may possibly have also a larger diameter.

Figure 8A:
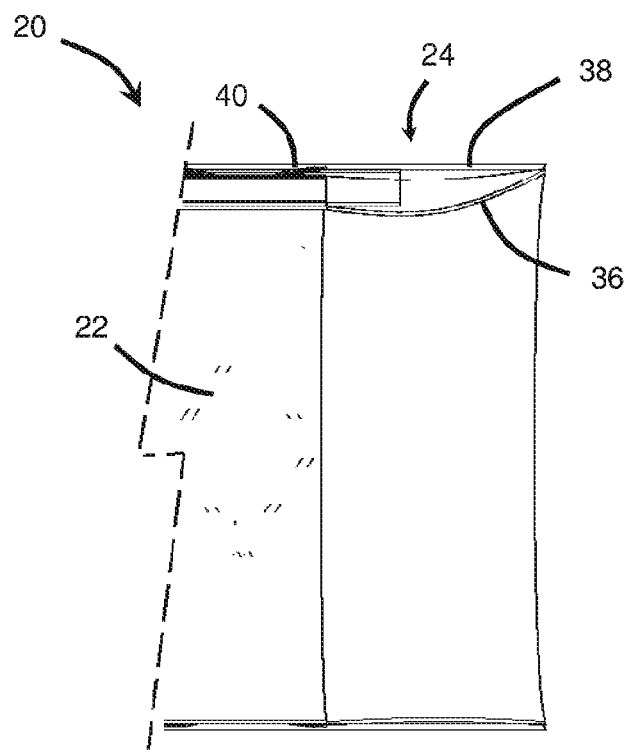
Figure 8B:
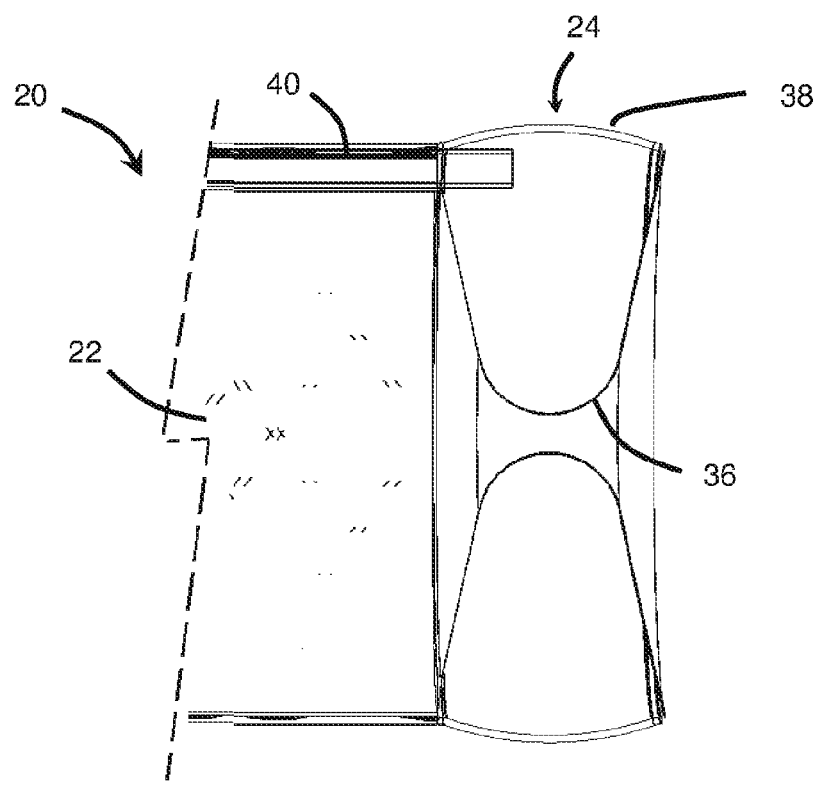

Attention is drawn to FIGS. 8A and 8B schematically illustrating cross sectional views of a catheter embodiment having an inflatable member 24 embodiment shown including inner and outer membranes or films 36, 38 configured here for being inflated by an inflation lumen 40 in the optional form of an inflation tube. The films 36, 38 may be continuously formed along the catheter also in regions not including the inflatable member 24 and possibly heat sealed in the periphery to form a distinct inflatable member 24 adjacent the catheter's distal end. In an embodiment, at least one of the films 36, 38 forming of inflatable member 24 may be different from other films possibly formed along the catheter's body.

Figure 9:
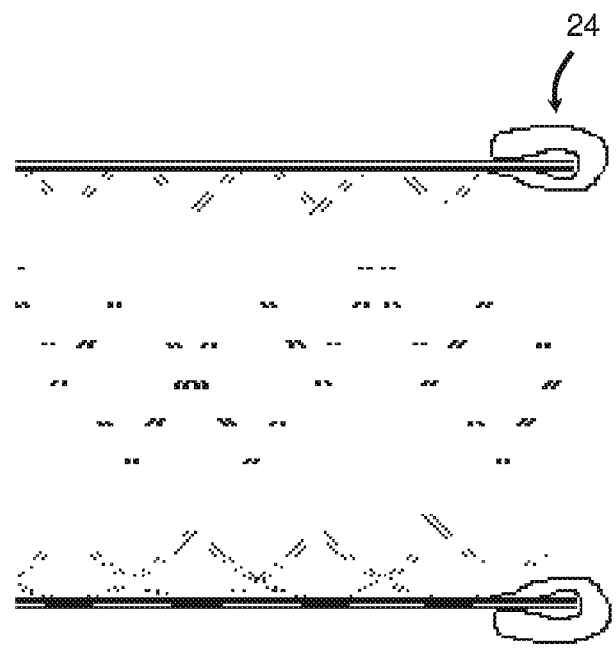

Inflation lumen 40 extends along catheter 20 and communicates with an area between the membranes in order to communicate/provide/deliver pressurized inflation media configured to activate inflation of member 24 from the uninflated state seen in FIG. 8A to the inflated state seen in FIG. 8B. The mesh of body 22 may be encapsulated in between the membranes 36, 38 e.g. to provide axial support for the membranes/films during insertion of e.g. an obstruction and/or stent retriever into the casing's internal lumen. In an aspect of the invention, inner film 36 may be of or include fluoropolymer film layer(s) in order to reduce insertion forces applied by objects such as an obstruction and/or stent retriever being urged in the proximal direction into casing 20. Instead (or in addition) to encapsulating the mesh of body 22 in between the membranes/films, one or more of films in the area forming the inflatable member may be initially folded back as illustrated in FIG. 9 to avoid/limit contact with objects being urged proximally into casing 20, so that only upon inflation, the inflatable member 24 assumes a state generally similar to that seen e.g. in FIG. 8B. The inflatable member 24 may be formed from films/ membranes or be a distinct balloon attached to the distal end of the catheter.

In an aspect of the invention, at least some catheter and/or casing embodiments of the present invention may be designed to perform plugging of the catheter's distal end with inflatable membrane(s) or balloon(s) that are configured to apply minimal outer radial forces upon the blood vessel wall. With respect to the embodiment shown in FIG. 8 this may be accomplished by choosing the inner membrane/film 36 to be more compliant than the outer membrane 38, possibly choosing the inner film to be of a semi-compliant or compliant material and the outer film/membrane to be non-compliant. By way of an example, the inner more compliant membrane/film may be chosen to be from at least one of: urethane, silicone (or the like); and the outer less compliant (e.g. non-compliant) membrane/film may be chosen to be from at least one of: PET, polyurethane, fluoropolymers (PTFE, FEP) (or the like).

In such embodiments, the outer less compliant membrane/ film 38 may substantially resist outer radial movement while the inner more compliant membrane/film may be urged to inflate inwards to plug the catheter's lumen, for example while the outer film 38 exhibits minimal or substantial no radial outer directed inflation—thus creating non or minimal outer directed forces (and consequently potential damage) upon a blood vessel wall within which such inflatable member 24 is inflated (see, e.g., lumen wall 27 in FIG. 2B).

In an aspect of the invention, and with respect to a discussion made herein below in the context of FIG. 13 of expansion of inflatable member(s) along path(s) of least resistance; initial expansion of e.g. a compliant or semi-compliant balloon, material and/or film/membrane in a direction of least resistance, e.g. inwards (as e.g. in FIG. 8) may take place until it makes contact with a boundary of e.g. another side of the catheter's peripheral wall or other inflatable members (if there are several) or other portions of an inflatable members (as e.g. in FIG. 8 embodiment). At that time-point a pressure curve representing pressure within the inflatable member(s), for example displayed to a physician and/or monitored by a controller coupled or in communication with the catheter or system including the catheter, typically increases relative steeply with continued inflation. For purpose of encouraging contact between an inflatable member and a limiting boundary, the inflatable member(s) may for example be nested within an inner wall of a catheter's body rather than protruding from it open end.

In an embodiment of the invention, a physician operating a catheter embodiment of the invention and/or a controller configured to regulate inflation of inflatable members(s) included in such embodiment, may be configured to identify such pressure rise and determine if the monitored pressure exceeds a pre-defined pressure value (for example <about 1 atm) that has been determined e.g. in bench studies, as required to occlude the catheter's lumen. If pressure has been found to exceed or reach this pre-defined pressure value, a conclusion may be reached that the inflatable member(s) reached an occlusive state of the lumen and further inflation may be terminated in order to possibly avoid inflation, inter alia, in radially outward directions that may cause damage to a blood vessel.

Figure 10:
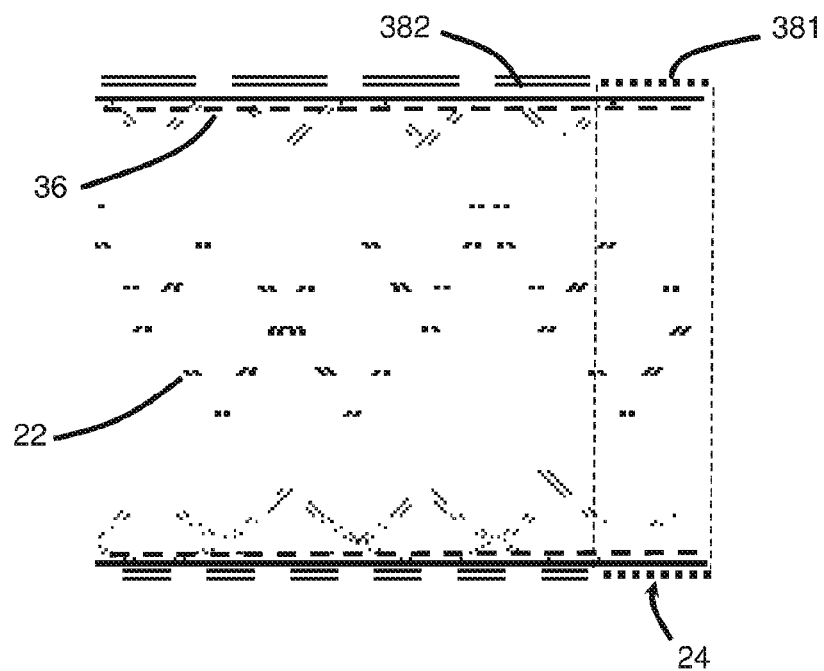

With attention drawn to FIG. 10, a catheter embodiment is illustrated having an inflatable member 24 formed from an inner compliant type film 36 possibly attached to peripheral inner side the catheter's body 22, possibly along an extension of the catheter also proximal to the inflatable member 24, and an outer less compliant film 381 located substantially only at a distal end to the body's mesh configured to form the inflatable member 24.

Since a non-compliant film/membrane may reduce compliance and consequently flexibility and/or ability to of the catheter's body 22 to expand (for example self-expand)— provision of a non-compliant film 381 substantially only at a portion forming the inflatable member 24 may minimize such reduction in compliance of the catheter's body. At locations proximal to the inflatable member 24, in addition to the semi-compliant and/or compliant film 36 formed on the inner side of the catheter's body, an outer film 382 may be formed/located on an outer side of the body. Outer film 382 may be similar in compliance to inner film 36 i.e. formed from semi-compliant or compliant material and may be of the same or different material as inner film 36.

In principle and with respect to at least most embodiments of the invention, attachment of films/membranes/balloons to each other and/or to portions of a catheter (e.g. a body's mesh) may be by thermal bonding (e.g. ultrasonic welding, laser welding, etc.) depending on material properties. Adhesive bonding may also be applicable (typically UV activated). In addition, pneumatic pressures required for inflating at least most inflatable member embodiments of the invention may typically be in a range of about 1-3 atmospheres depending on design and requirements. Also, in at least some embodiments, inflatable member(s) may initially (prior to first inflation) start from a deflated state (possibly with creases/pleats on inner and/or outer sides) that is held deflated by vacuum in order to help in retaining a packaging shape/state.

Figure 11:
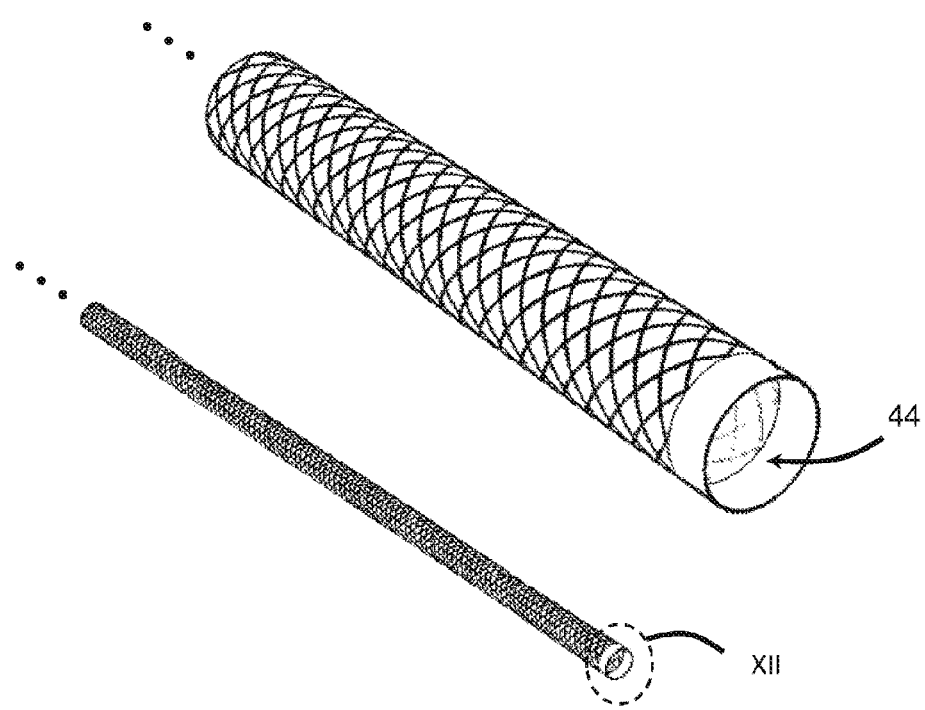
FIG. 11 schematically shows expanded and non-expanded states of at least certain catheter embodiments.

Attention is drawn to FIG. 11 illustrating non-expanded and expanded states of a catheter 12 according to at least most embodiments of the invention. The non-expanded state seen in the lower side of the figure, possibly being a state where a preferable self-expanding body of a catheter embodiment is held non-expanded by a sheath (not shown) during e.g. delivery of the catheter to a position where it is to be deployed (such as in FIG. 1C). The expanded state illustrated in the upper side of the figure representing a deployed state of the catheter (such as in FIG. 1D), possibly after removal of a sheath in a self-expanding catheter embodiment. An outer diameter of the catheter in the non-expanded state (lower side of figure) in a non-binding example may be about 1 millimeter (possibly including also wall thickness of the sheath constraining such non-expanded state) and in an expanded state may reach about 2-6 millimeter and possibly slightly more.

Figure 12:
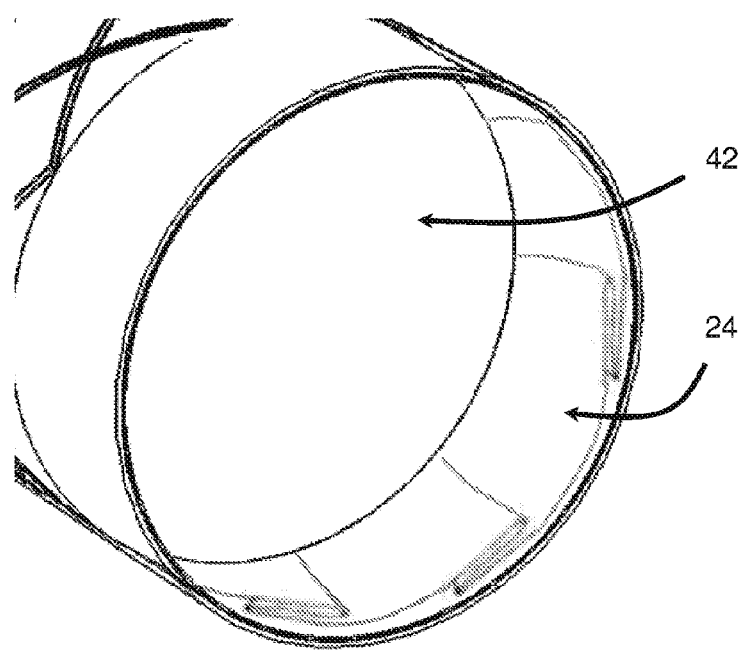
FIG. 12 schematically shows an enlarged view of a portion of the unexpanded state in FIG. 11.

In embodiments of the invention, where a catheter's inflatable member 24 includes inner and/or outer films/ membranes or an inflatable balloon(s); such films/membranes or balloon(s) may reduce compliance of the body (mesh) and consequently the catheter's ability to expand or fully expand. Thus, in at least some embodiments of the invention, the films/membranes or balloon(s) may be folded e.g. in flat cut shapes to increase compliance and ability to expand. Attention is drawn to FIG. 12 illustrating an enlarged view of the catheter's distal portion in a non-expanded state of the catheter, exemplifying such folds, here formed as pleats of the inflatable member 24. In embodiments where the inflatable member 24 is formed from inner and/or outer films/membranes, these folds may be formed on the membranes/films.

Further apparent from the embodiment of FIG. 12 is that a catheter according to at least some embodiment of the invention, in a non-expanded state includes at least a small inner void 42 configured for passage of a wire (not shown) upon which the catheter is delivered in a non-expanded state to a position within a body vasculature where it is designed to be deployed. This void 42 being configured to form in a catheter's expanded state, the catheter's inner lumen 44 through which e.g. devices such as a stent retriever may pass and/or obstructions blocking a blood vessel may be removed.

Figure 13:
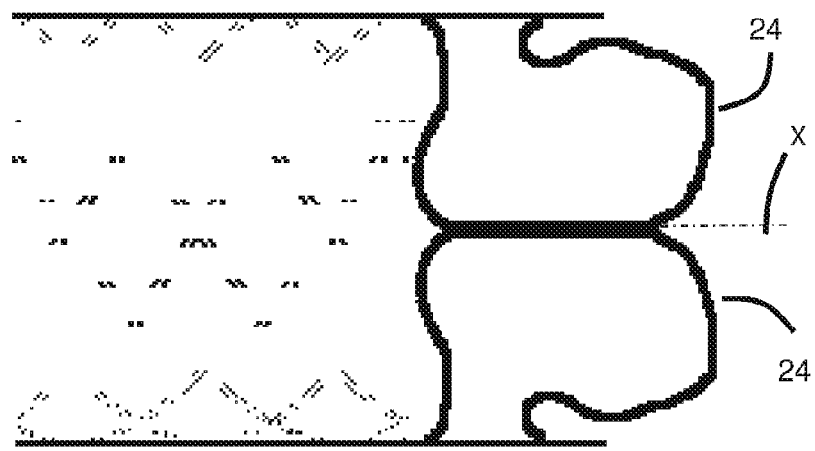

Attention is drawn to FIG. 13 illustrating a catheter embodiment including two independent inflatable members 24 that inflate separately. In the context of the embodiment of FIG. 13, a broad aspect applicable to at least certain embodiments of the invention can be seen, where an inflatable member(s) once meeting a boundary, here meeting an opposing member, is/are configured to continue expansion in a direction taken along a path of least resistance. In the example here shown, such path of least resistance is shown being directed generally along the catheter's axis, here in a distal axial direction. Thus, avoidance or limitation of formation of outer directed expansion of inflatable member(s) (and consequently potential damage to blood vessels) may be facilitated by provision of such "free" paths for the inflatable member(s) to continue expansion after meeting a boundary. Preferably inflatable members made of semi-compliant or compliant materials (preferably semi-compliant or compliant elastomeric materials) may have an increased tendency to bulge-out along such "free" paths and not continue expansion along a pre-designed path of expansion, as may be the case with less compliant materials such as non-compliant materials.

Figure 14:
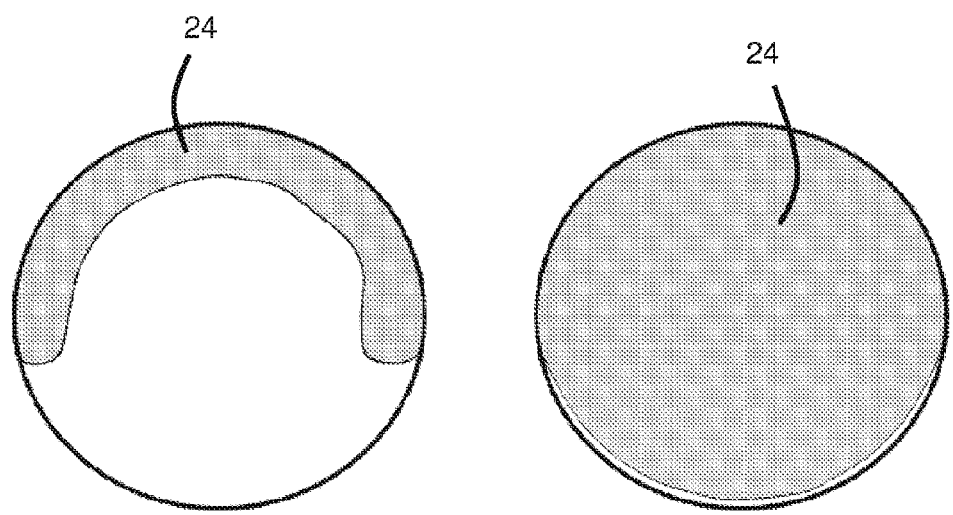

In FIG. 14 an additional catheter embodiment is shown illustrating from an end axial view use of a semicircular inflatable member 24, in the left hand side of the figure being shown in an uninflated state, and in the right hand side in an inflated state. Having the inflatable member on half of the circular structure may allow for less material in the inflatable member. An embodiment where the inflatable member 24 is formed from inner and outer films/membranes (as e.g. in FIG. 8) may include an outer film of relatively rigid non-compliant nature and an inner film, possibly of semi-compliant or compliant nature being configured to push towards the opposite side, filling the catheter's inner lumen e.g. 44.

In an embodiment of the invention, the inflatable member of FIG. 14 may be compliant (possibly from urethane material) to accommodate range of blood vessel diameters. Here urethane or nylon inflatable member materials (possibly polyurethane (e.g. santoprene, pellethane tradenames of Exxon Mobil Corporation and the Lubrizol Corporation, respectively), LPDE/LLDPE) may be thermally welded, adhesively bonded, or laser welded for attachment e.g. to a body's mesh. Inflatable member material may have a wall thicknesses possibly of about 0.025-0.05 millimeters.

Figure 15A:
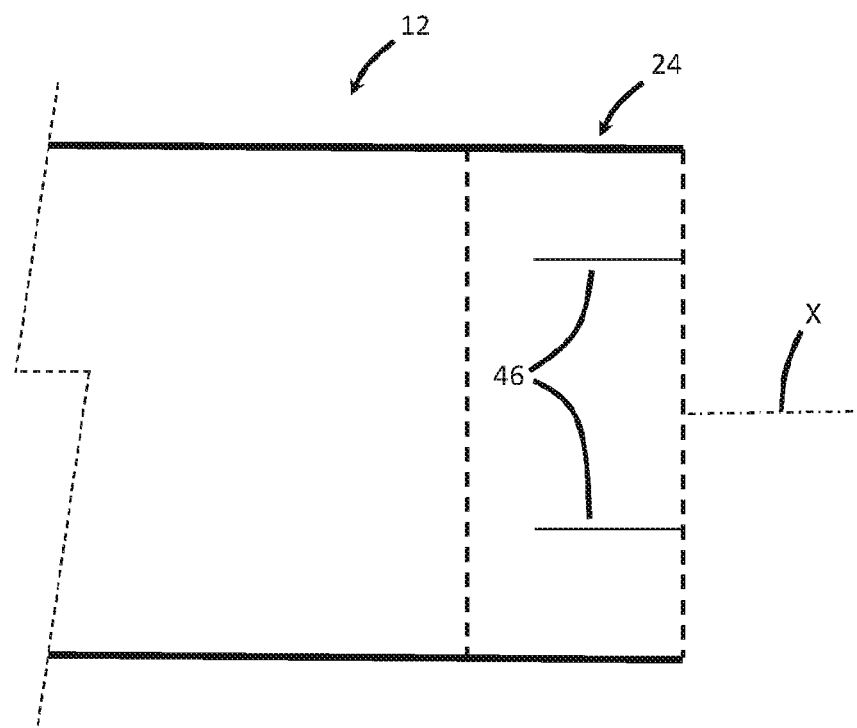
Figure 15B:
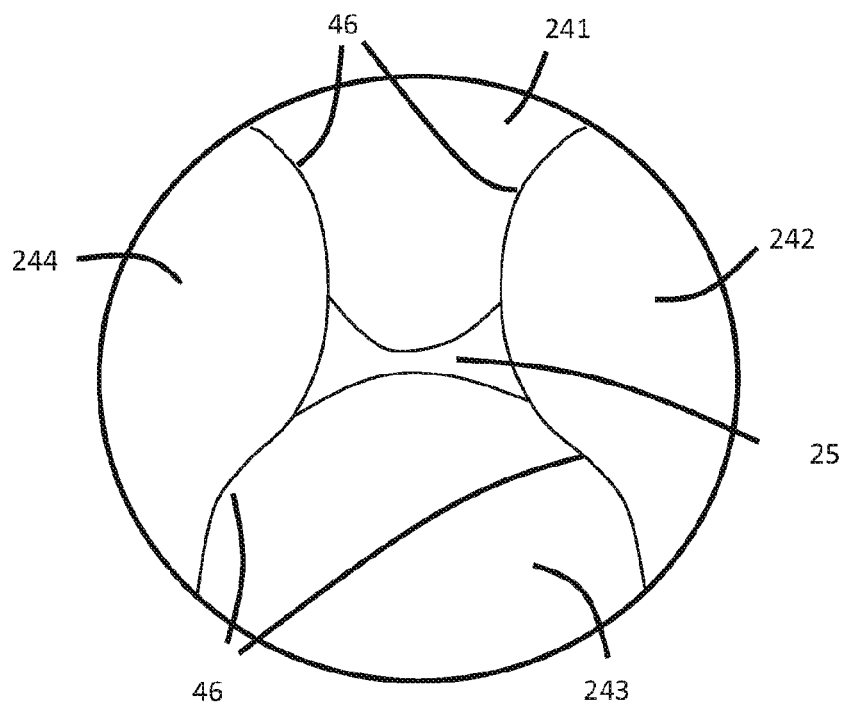

Attention is drawn to FIGS. 15A and 15B, respectively, illustrating side and front views of a catheter 12 according to an embodiment of the invention. Inflatable member 24 is here of a dual layer type, such as member 24 in FIG. 8 that includes dual layers there of the films 36, 38. The inflatable member in the example here is also shown generally being of a "holeless donut" type where portions of the member 24 are configured to meet itself and substantially seal at a center 25 of the "holeless donut".

In an embodiment of the invention, the inflatable member 24 may include seam portions 46, here possibly formed by heat sealing, that generally extend in a direction of the catheter's axis X (at least when viewed in a deflated state of the inflatable member) that are configured to create smaller inflatable segments, here four such segments 241, 242, 243, 244; that all inflate as one towards the center. The seam portions 46 for example form seams along which inner and outer parts of the inflatable member become connected to each other, e.g. by heat bonding.

For example, in embodiments of an inflatable member 24 formed from inner and outer films/membranes (e.g. 36, 38 in FIG. 8) such connection may be between these films. Segments 241-244 may for example be in fluid communication one with the other e.g. to permit inflation by a single inflation lumen. In addition, provision of such seam portions may assist in some cases to better fill a center 25 towards which the portions inflate in comparison to a case where the inflatable member is one large member.

Figure 16:
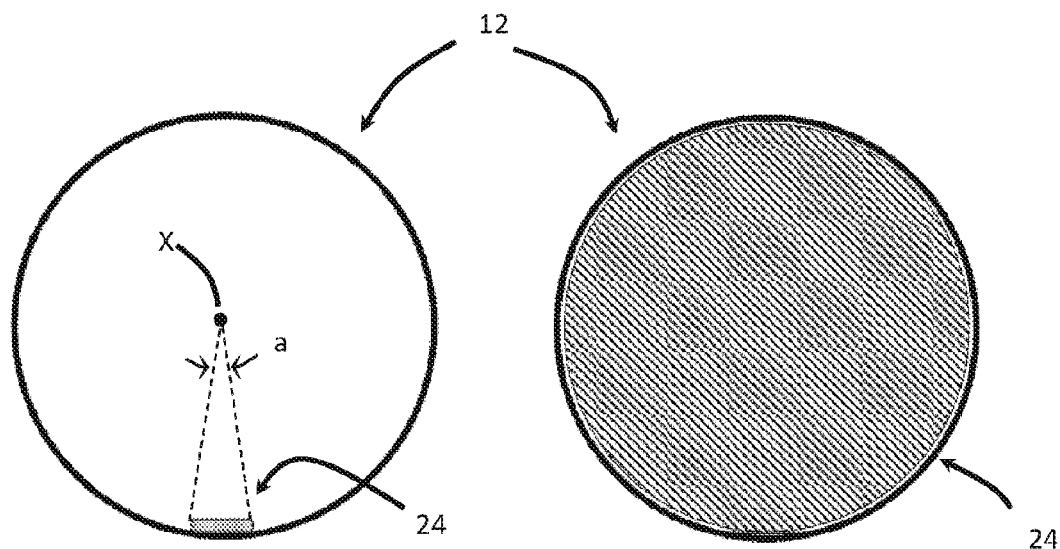

Attention is drawn to FIG. 16 schematically illustrating an embodiment of a catheter 12 including a possible form of an inflatable member 24. In the left hand side of the figure, member 24 is illustrated in a deflated state and in the right hand side of the figure in an inflated state. Inflatable member 24 in this embodiment, as illustrated is shown relatively small in dimension in the deflated state as a so-called 'single point' on the inner lumen circumference and configured for inflation to occlude the whole lumen of the catheter, possibly due to its very compliant nature.

In an embodiment, the so-called 'single point' nature of the inflatable member 24 may be defined as following. In a cross section perpendicular to axis X of the catheter and passing through the inflatable member, the inflatable member 24 in a deflated state may extend along a short segment of a periphery of the catheter's lumen that has an angular extension 'a' that is less than about 30 degrees and preferably less than about 15 degrees. Such inflatable member 24, possibly due to the compliant nature of its material, may be inflated to occlude at least most of the catheter's lumen. Such inflatable member although not illustrated may be held in the so-called 'single point' state at least in certain embodiment while being folded upon itself e.g. by including folds or pleats.

Figure 17:
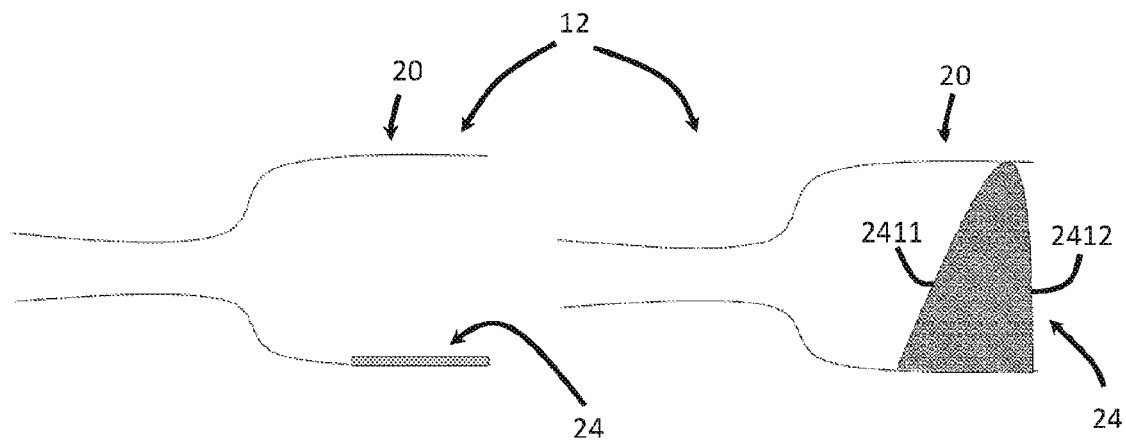

With attention additionally drawn to FIG. 17, possible views of a catheter embodiment having an inflatable member 24 generally similar to that shown in FIG. 16 is illustrated. In the left hand side of FIG. 17 a catheter having an inflatable member in a deflated state possibly representative of the deflated state in the left hand side of FIG. 16 is illustrated; and an inflated state in the right have side of FIG. 17 possibly being representative of the inflated state in the right hand side of FIG. 16. In an embodiment of the invention, a proximal facing side or portion 2411 of the inflatable member 24 in this example may be formed from thicker and/or less compliant material than a distal facing side 2412 of the inflatable member that may possibly be formed from thinner and/or softer and/or more compliant material, where both sides 2411, 2412 being defined in an inflated state of the member 24.

Figure 18:
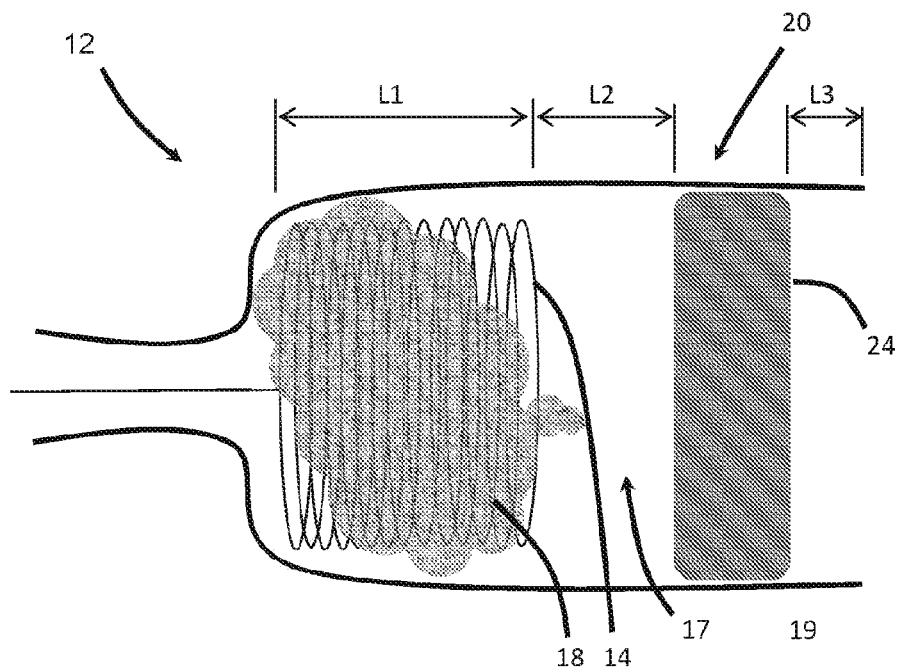

Attention is drawn to FIG. 18 schematically illustrating an embodiment of a catheter 12 including a possible form of an inflatable member 24 of any one of the embodiments described herein—here illustrated in an inflated state. In the provided illustration, catheter 12 is shown including matter such as an obstruction 18 located in the catheter's casing 20, where possibly the matter has been introduced into the catheter by means of a retrieval device 14 such as that including a so-called stent retriever.

In the shown example, catheter 12 is illustrated being sized to accommodate the matter e.g. 18 (possibly with a retrieval device that introduced same into the catheter), at a proximal area of the catheter's casing. In catheter embodiments including a neck portion, this proximal area may start at a vicinity of the merge between the casing and neck and extend from there in a distal direction. An axial extension L1 of such matter with or without a retrieval device may be up to a few centimeters possibly up to about four centimeters. In the shown example, also an optional gap 17 between a distal side of the matter (with or without the retrieval device) and a proximal side of the inflatable member(s) 24 in its inflated state is illustrated here having an axial extension L2. An optional spacing 19 having an axial extension L3 is illustrated between a distal side of the inflated inflatable member(s) 24 and a distal end of the catheter.

Figure 19:
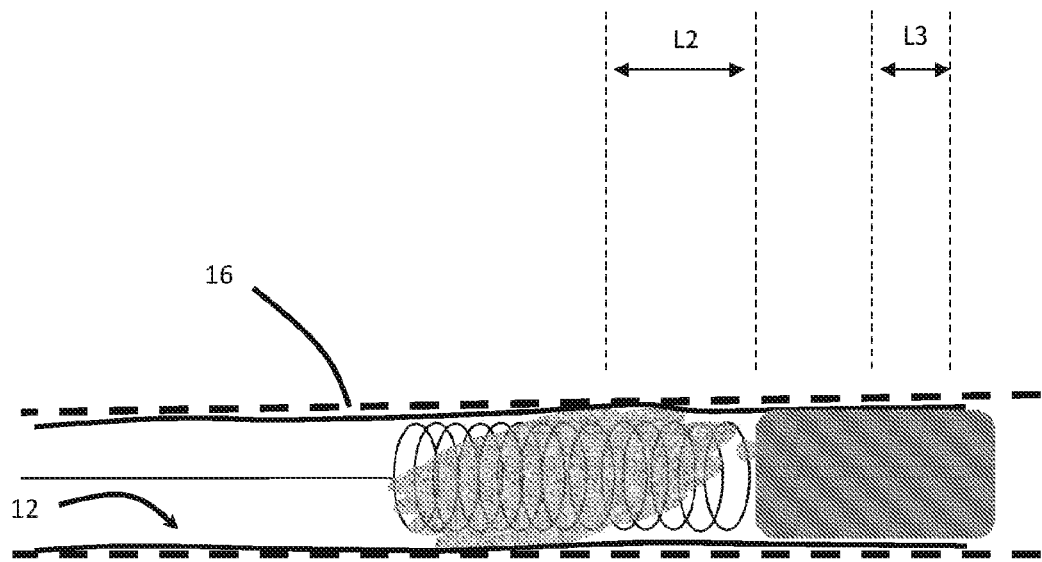

Attention is drawn to FIG. 19 illustrating a possible appearance of the catheter of FIG. 18 when or after being urged into a guide catheter (GC) or long sheath (LS) 16 such as that illustrated in FIGS. 1A to 1I. Possibly, the illustration seen in FIG. 19 represents a procedural step generally similar to that illustrated in FIG. 1I where the catheter has 'disappeared' into the GC or LS.

During this step, as illustrated in FIG. 19, the removed matter within the catheter may be 'squashed' and urged to extend in an axial direction within the catheter such as also in a distal axial direction. In catheter embodiments that are sized to include a gap 17, this axial extension may be accommodated within the axial extension L2 of gap 17. In addition, the inflatable members(s) may also be 'squashed' and urged to extend in an axial direction within the catheter such as also in a distal axial direction. In catheter embodiments that are sized to include a spacing 19, this axial extension may be accommodated at least partially within the axial extension L3 of spacing 19, where here the inflatable member(s) 24 is illustrated possibly bulging distally out beyond the catheter's distal end or tip.

Introducing a catheter into a GC or LS with removed matter within it, in at least certain catheter embodiments and/or procedures, may in some cases urge the matter to be extruded in a distal axial direction out of the catheter. Thus, in some cases, sizing the catheter to include a gap 17 and/or spacing 19 may assist in limiting this possible occurrence by providing one or more 'buffer' zones, where the 'extruded' matter and/or the 'squashed' inflatable member(s) may be housed. In embodiments where the inflatable member(s) are configured to include compliant material, the urging of the inflatable member(s) into e.g. spacing 19 may be provided with limited resistance due to friction e.g. against the body of the catheter and/or with limited increase in radial outer forces acting on the blood vessel where the procedure is taking place.

In the discussion herein, reference to non-compliant, semi-compliant and compliant materials may be defined as following at least when assessed in normal body temperature.

A non-compliant material as referred to herein may be defined as having a Burst Strength of about 15-400 psi (about 1-27 atm—defining a working range), a Rated Burst Pressure (i.e. pressure at which 99.9% of balloons can survive with 95% confidence) of about 265 to 325 psi (about 18-22 atm), a diameter growth of about 0-10% (within the working range) and may be made of materials such as PET, Nylon 12 (or the like).

A semi-compliant material as referred to herein may be defined as having a Burst Strength of about 15-300 psi (about 1-20 atm—defining a working range), a Rated Burst Pressure of about 75 to 265 psi (about 5 to 18 atm), a diameter growth of about 10-20% or more (within the working range) and may be made of materials such as polyamides, PET, Nylon12, Pebax, Polyurethane (or the like).

A compliant material as referred to herein may be defined as having a Burst Strength of about 1.5-30 psi (about 0.1-2 atm—defining a working range), a diameter growth of about 20-200% or more (within the working range), and may be made of materials such as Polyurethane, Pebax, Silicone, nylon elastomers (or the like).

Inflatable member(s) of the examples herein described may be formed by a blow-molding process and in some cases, also by a dip molding process. The above mentioned tests of 'Burst Strength', 'diameter growth' and/or 'Rated Burst Pressure' may be performed, for example, while utilizing for testing a Crescent Burst Tester or Interface Burst Tester (or the like) and a laser measurement system such as a 'glass logic' Laser Micrometer (or the like) and/or when performing the tests under the ISO 10555, FDA guidelines (e.g. ISO 10555-4). Compliance (e.g. non-compliant, semi-compliant and/or compliant as defined herein) at least in some cases may be defined from the molded shape of a tested inflatable member to what it can safely expand to.

For instance, a 5 mm spherical inflatable member made in polyurethane may be considered compliant and could likely inflate to at least 10 mm spherical. This would be 100% increase in compliance. A Pebax 5 mm inflatable member for example may be considered semi-compliant. This type inflatable member could likely inflate from its molded 5 mm diameter to 6 mm diameter, and thus would be a 20% increase in compliance. An inflatable member exerting more than 200% in diameter growth in a non-binding example may be or include silicone or latex (or similar nature materials known in the art), and in certain cases may be formed by a dip molding process.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

Further more, while the present application or technology has been illustrated and described in detail in the drawings and foregoing description, such illustration and description are to be considered illustrative or exemplary and non-restrictive; the technology is thus not limited to the disclosed embodiments. Variations to the disclosed embodiments can be understood and effected by those skilled in the art and practicing the claimed technology, from a study of the drawings, the technology, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures can not be used to advantage.

The present technology is also understood to encompass the exact terms, features, numerical values or ranges etc., if in here such terms, features, numerical values or ranges etc. are referred to in connection with terms such as "about, ca., substantially, generally, at least" etc. In other words, "about 3" shall also comprise "3" or "substantially perpendicular" shall also comprise "perpendicular". Any reference signs in the claims should not be considered as limiting the scope.

Although the present embodiments have been described to a certain degree of particularity, it should be understood that various alterations and modifications could be made without departing from the scope of the invention as hereinafter claimed.

The invention claimed is:

1. A catheter positionable within a body vasculature, the catheter comprising an expandable body formed from a wire braid, said expandable body having a distal end opening into a lumen when said expandable body is expanded and a segmented balloon having a plurality of separately inflatable pie segments attached to said distal end of said expandable body and being configured for at least partially closing an opening at said distal end when inflated.

2. The catheter of claim 1, wherein said expandable body is self-expanding.

3. The catheter of claim 1, wherein each of said inflatable segments of said balloon is configured to inflate into said lumen.

4. The catheter of claim 1, wherein an inner surface of each of said inflatable segments of said balloon facing said distal end is fabricated from a material more compliant than that of an outer surface of each of said inflatable segments of said balloon.

5. The catheter of claim 1, wherein said expandable body is about 2 to about 6 millimeters in diameter when expanded.

6. The catheter of claim 1, wherein said wire braid is at least partially covered.

7. The catheter of claim 6, wherein inner and outer surfaces of said braid are covered.

8. The catheter of claim 6, wherein said cover enables said expandable body to apply suction.

9. The catheter of claim 8, further comprising a vacuum source in communication with said lumen of said expandable body.

10. A method for retrieving material from a body vasculature comprising:
    (a) positioning within the vasculature a catheter including an expandable body having a distal end opening into a lumen when said expandable body is expanded and a segmented balloon having a plurality of separately inflatable pie segments attached to said distal end of said expandable body and being configured for at least partially closing an opening at said distal end when inflated;
    (b) drawing the material into said lumen; and
    (c) inflating each of said inflatable pie segments of said balloon to at least partially close said distal end of said expandable body.

11. The method of claim 10, wherein (b) is affected using suction.

12. The method of claim 10, wherein each of said inflatable segments of said balloon inflates into said opening.

* * * * *